(12) United States Patent
Eisenbach-Schwartz et al.

(10) Patent No.: US 8,716,228 B2
(45) Date of Patent: May 6, 2014

(54) GPR54 AGONISTS OR ANTAGONISTS FOR TREATMENT OF DISEASES PRESENTING BEHAVIORAL ABNORMALITIES

(75) Inventors: Michal Eisenbach-Schwartz, Rehovot (IL); Gil M Lewitus, Rehovot (IL); Michal Cardon-Yaakov, Rehovot (IL); Noga Ron-Harel, Rehovot (IL)

(73) Assignee: YEDA Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/322,713

(22) PCT Filed: May 27, 2010

(86) PCT No.: PCT/IL2010/000422
§ 371 (c)(1),
(2), (4) Date: Feb. 13, 2012

(87) PCT Pub. No.: WO2010/137022
PCT Pub. Date: Dec. 2, 2010

(65) Prior Publication Data
US 2012/0135935 A1 May 31, 2012

Related U.S. Application Data

(60) Provisional application No. 61/181,422, filed on May 27, 2009.

(51) Int. Cl.
*A61K 38/00* (2006.01)

(52) U.S. Cl.
USPC ........ 514/17.5; 514/17.6; 514/17.7; 514/21.3

(58) Field of Classification Search
None
See application file for complete search history.

(56) References Cited

U.S. PATENT DOCUMENTS

| | | | |
|---|---|---|---|
| 6,699,965 B1 | 3/2004 | Watanabe et al. |
| 6,800,611 B2 | 10/2004 | Fujii et al. |
| 7,314,754 B2 | 1/2008 | Watanabe et al. |
| 2002/0106766 A1 | 8/2002 | Elshourbagy et al. |
| 2006/0015954 A1 | 1/2006 | Aparicio et al. |
| 2006/0241051 A1 | 10/2006 | Kitada et al. |
| 2011/0003978 A1 | 1/2011 | Ralph et al. |
| 2011/0214189 A1 | 9/2011 | Gaitanaris et al. |

FOREIGN PATENT DOCUMENTS

| | | |
|---|---|---|
| JP | 2010083793 A | 4/2010 |
| WO | WO 03003983 A2 | 1/2003 |
| WO | WO 2004063221 A1 | 7/2004 |
| WO | WO 2004087622 A1 | 10/2004 |
| WO | WO 2006001499 A2 | 1/2006 |
| WO | WO 2008050897 A1 | 5/2008 |
| WO | WO 2009047513 A2 | 4/2009 |
| WO | WO 2009139298 A1 | 11/2009 |
| WO | WO 2010033224 A1 | 3/2010 |

OTHER PUBLICATIONS

Castellanos, et al., "Sensorimotor Gating in Boys with Tourette's Syndrome and ADHD: Preliminary Results", Society of Biological Psychiatry, 1996, pp. 33-41, vol. 39.

Alamed, et al., "Two-day radial-arm water maze learning and memory task; robust resolution of amyloid-related memory deficits in transgenic mice", Nature Protocols, Nov. 9, 2006, pp. 1671-1679, vol. 1, No. 4.

Binder, et al., "Enhanced Neurotensin Neurotransmission is Involved in the Clinically Relevant Behavioral Effects of Antipsychotic Drugs: Evidence from Animal Models of Sensorimotor Gating", The Journal of Neuroscience, Jan. 15, 2001, pp. 601-608, vol. 21, No. 2.

Chou, et al., "The Immune Response of Lewis Rats to Peptide 68-88 of Guinea pig Myelin Basic Protein", The Journal of Immunology, Oct. 1979, pp. 1540-1543, vol. 123, No. 4.

Cryan, et al., "The tail suspension test as a model for assessing antidepressant activity: Review of pharmacological and genetic studies in mice", Neuroscience and Biobehavioral Reviews, 2005, pp. 571-625, No. 29.

Kumar, "Testosterone for schizophrenia (Review)", The Cochrane Collaboration, 2010, pp. 1-31, No. 1.

Gil-Ad, et al., "Abnormal Growth Hormone Response to LRH and TRH in Adolescent Schizophrenic Boys", Am J Psychiatry, Mar. 1981, pp. 357-360, vol. 138, No. 3.

Gottsch, et al., "A Role for Kisspeptins in the Regulation of Gonadotropin Secretion in the Mouse", Endocrinology, Sep. 2004, pp. 4073-4077, vol. 149, No. 9.

Hauben, et al., "Vaccination with Dendritic Cells Pulsed with Peptides of Myelin Basic Protein Promotes Functional Recovery from Spinal Cord Injury", The Journal of Neuroscience, Sep. 24, 2003, pp. 8808-8819, vol. 23, No. 25.

Kulkarni, et al., "Estrogen—a potential treatment for schizophrenia", Schizophrenia Research, 2001, pp. 137-144, vol. 48.

Niida, et al., "Design and synthesis of downsized metasin (45-87) analogs with maintenance of high GPR54 agonistic activity", Bioorganic & Medicinal Chemistry Letters, 2006, pp. 134-137, No. 16.

Ohtaki, et al., "Metastasis suppressor gene KiSS-1 encodes peptide ligand of a G-protein-coupled receptor", Nature, May 31, 2001, pp. 613-617, vol. 411.

(Continued)

*Primary Examiner* — Olga N Chernyshev
(74) *Attorney, Agent, or Firm* — Browdy and Neimark, PLLC

(57) ABSTRACT

Use of a GPR54 agonist or antagonist for the treatment of a disease or disorder presenting behavioral abnormalities associated with impairment of sensory gating function, and/or for treatment of depression, and/or for improving cognitive function is disclosed. In particular, the invention relates to the use of kisspeptin or a peptide thereof for the treatment of schizophrenia.

13 Claims, 11 Drawing Sheets

(56) References Cited

OTHER PUBLICATIONS

Ornitz, et al., "Prestimulation-Induced Startle Modulation in Attention-Deficit Hyperactivity Disorder and Nocturnal Enuresis", Psychophysiology, Jul. 1992, pp. 437-451, vol. 29, No. 4.

Piontkewitz, et al., Clozapine Administration in Adolescence Prevents Postpubertal Emergence of Brain Structural Pathology in an Animal Model of Schizophrenia, 2009, pp. 1038-1046, vol. 66.

Rothermundt, et al., "Review of Immunological and Immunopathological Findings in Schizophrenia", Brain, Behavior, and Immunity, 2001, pp. 319-339, vol. 15.

Seminara, et al., "The GPR54 Gene as a Regulator of Puberty", The New England Journal of Medicine, Oct. 23, 2003, pp. 1614-1627, vol. 349, No. 17.

Soreni, et al., "Beneficial Effects of Gonadotropin-Releasing Hormone Analogue Treatment on Positive and Negative Symptoms of Schizophrenia: A Case Report", J Clin Psychiatry, Jul. 2004, pp. 1020-1021, vol. 65, No. 7.

Steru, et al., "The tail suspension test: A new method for screening antidepressants in mice", Psychopharmacology, 1985, pp. 367-370, vol. 85.

Strauss, et al., "Brain-derived neurotrophic factor variants are associated with childhood-onset mood disorder: confirmation in a Hungarian sample", Molecular Psychiatry, 2005, pp. 861-867, vol. 10.

Swerdlow, et al., "A Preliminary Assessment of Sensorimotor Gating in Patients with Obsessive Compulsive Disorder", Biological Psychiatry, 1993, pp. 298-301, vol. 33.

Swerdlow, et al., "Impaired prepulse inhibition of acoustic and tactile startle response in patients with Huntington's disease", Journal of Neurology, Neurosurgery and Psychiatry, 1995, pp. 192-200, vol. 58.

Swerdlow, et al., "Using and Animal Model of Deficient Sensorimotor Gating to Study the Pathophysiology and New Treatments of Schizophrenia", Schizophrenia Bulletin, 1998, pp. 285-301, vol. 24, No. 2.

Swerdlow, et al., "Startle Gating Deficits in a Large Cohort of Patients with Schizophrenia", Arch Gen Psychiatry, Dec. 2006, pp. 1325-1360, vol. 63.

Tomita, et al., Structure-activity relationship study on small peptidic GPR54 agonists, Bioorganic & Medicinal Chemistry, 2006, pp. 7595-7603, vol. 14.

Ziv, et al., "Immune cells contribute to the maintenance of neurogenesis and spatial learning abilities in adulthood", Nature Neuroscience, Feb. 2006, pp. 268-275, vol. 9, No. 2.

Zuckerman, et al., "Immune Activation During Pregnancy in Rats Leads to a PostPubertal Emergence of Disrupted Latent Inhibition, Dopaminergic Hyperfunction, and Altered Limbic Morphology in the Offspring: A Novel Neurodevelopmental Model of Schizophrenia", Neuropsychopharmacology, 2003, pp. 1778-1789, vol. 28.

Vuillermot, et al., "A Longitudinal Examination of the Neurodevelopmental Impact of Prenatal Immune Activation in Mice Reveals Primary Defects in Dopaminergic Development Relevant to Schizophrenia", The Journal of Neuroscience, Jan. 27, 2010, pp. 1270-1287, vol. 30, No. 4.

Curtis, et al., "A kisspeptin-10 analog with greater in vivo bioactivity than kisspeptin-10", Am. J. Physiol. Endocrinol. Metab., May 25, 2010, pp. 296-303, vol. 298.

Gutierrez-Pascual, et al., "In vivo and in vitro structure-activity relationships and structural conformation of kisspeptin-10-related peptides", Molecular Pharmacology Fast Forward., Apr. 29, 2009, 38 pages.

Arai, "The role of kisspeptin and GPR54 in the hippocampus", Peptides, 2009, pp. 16-25, vol. 30.

Cardon, et al., "Dysregulation of kisspeptin and neurogenesis at adolescence link inborn immune deficits to the late onset of abnormal sensorimotor gating in congenital psychological disorders", Molecular Psychiatry, 2010, pp. 415-425, vol. 15., No. 4.

Arai, et al, "Cancer Metastasis—Suppressing Peptide Metastin Upregulates Excitatory Synaptic Transmission in Hippocampal Dentate Granule Cells", J Neurophysiol, 2005, pp. 3648-3652, vol. 94.

Bilban, et al., "Kisspeptin-10, a KiSS-1/metastin-derived decapeptide, is a physiological invasion inhibitor of primary human trophoblasts", Journal of Cell Science, 2003, pp. 1319-1328, vol. 117, No. 8.

De Roux, et al., "Hypogonadotropic hypogonadism due to loss of function of the KiSS1-derived peptide receptor GPR54", PNAS, Sep. 16, 2003, pp. 10972-10976, vol. 100, No. 19.

Dhillo, et al, "Kisspeptin-54 Stimulates the Hypothalamic-Pituitary Gonadal Axis in Human Males", The Journal of Clinical Endocrinology & Metabolism, 2005, pp. 6609-6615, vol. 90, No. 12.

Kipnis, et al, "T cell deficiency leads to cognitive dysfunction: Implications for therapeutic vaccination for schizophrenia and other psychiatric conditions", PNAS, May 25,2004, pp. 8180-8185, vol. 101, No. 21.

Lee, et al., "KiSS-1, a Novel Human Malignant Melanoma Metastasis-Suppressor Gene", Journal of the National Cancer Institute, Dec. 4, 1996, pp. 1731-1737, vol. 88, No. 23.

Luque, et al., "Regulation of Hypothalamic Expression of KiSS-1 and GPR54 Genes by Metabolic Factors: Analyses Using Mouse Models and a Cell Line", Endocrinology, 2007, pp. 4601-4611, vol. 148, No. 10.

Tena-Sempere, "GPR54 and kisspeptin in reproduction", Human Reproduction Update, 2006, pp. 631-639. vol. 12, No. 5.

Zajac, et al., "Wheel Running and Environmental Enrichment Differentially Modify Exon-Specific BDNF Expression in the Hippocampus of Wild-Type and Pre-motor Symptomatic Male and Female Huntington's Disease Mice", Hippocampus, 2010, pp. 621-636, No. 20.

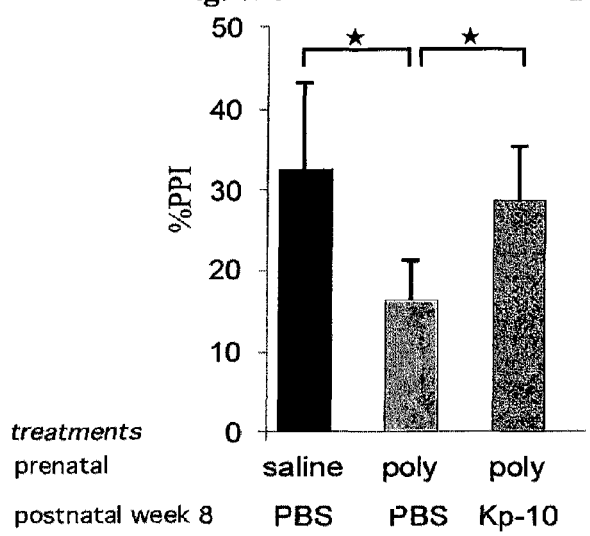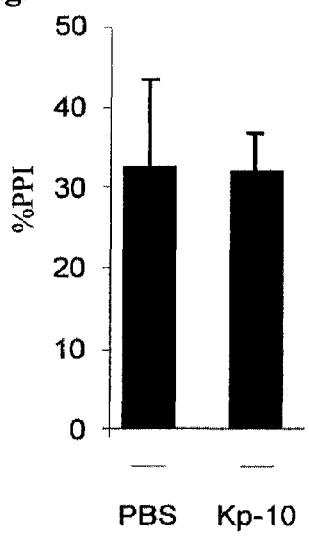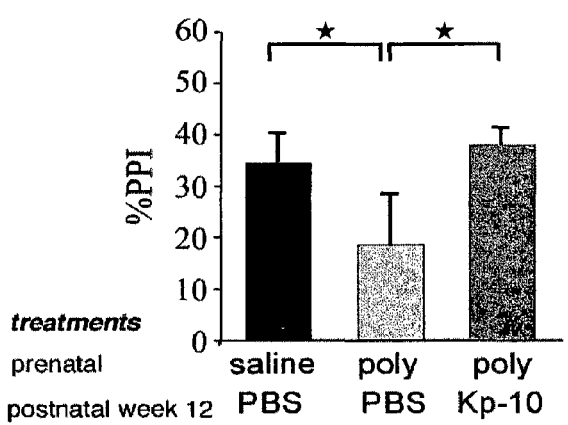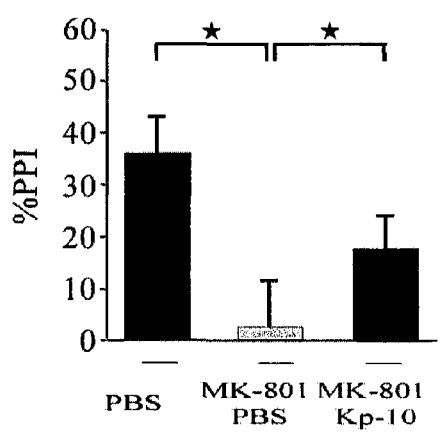

Immobile   Mobile

SCID

GPR54 AGONISTS OR ANTAGONISTS FOR TREATMENT OF DISEASES PRESENTING BEHAVIORAL ABNORMALITIES

FIELD OF THE INVENTION

The present invention is in the field of therapeutics and, in particular, it relates to treatment of diseases or disorders presenting behavioral abnormalities associated with impairment of sensory gating function such as schizophrenia and/or for treatment of depression, and/or for improving cognitive function.

BACKGROUND OF THE INVENTION

Sensory gating is a largely automatic process by which the brain adjusts its response to stimuli. When one stimulus is presented, there is a response; however, when the first stimulus is followed by a second stimulus soon after, the response to the second stimulus is blunted. This is an adaptive mechanism to prevent over stimulation that helps the brain focus on a stimulus among a host of other distracters, and contributes to the ability to selectively allocate attention to a significant event by silencing the background. The specific features of an individual's gating processes are viewed to be plastic, and governed by genetic and developmental processes, but also by environmental changes, neurochemical and hormonal state of the CNS. Sensory gating was shown to be disturbed in schizophrenia.

Prepulse inhibition (PPI), the phenomenon by which a low-intensity prepulse stimulus attenuates the response to a subsequent startle-eliciting stimulus, is used as a measurement of the sensory gating function (Swerdlow and Geyer, 1998). Impairment of PPI has been reported in several diseases including schizophrenia (Swerdlow et al., 2006), Huntington's chorea (Swerdlow et al., 1995), obsessive-compulsive disorder (Swerdlow et al., 1993), attention deficit hyperactivity disorder (ADHD) (Ornitz et al., 1992), and Tourette's syndrome (Castellanos et al., 1996). Importantly, PPI deficits are not unique to a single form of psychopathology. Therefore, it is often used as a paradigm for assessing the modulation of early information processing and for screening pharmacological interventions.

Schizophrenia is a complex and severe brain disorder with poorly defined etiology and pathophysiology, which affects approximately 1% of the world population. Although the risk factors that correlate with the disease are mostly congenital (i.e. genetic aberrations, prenatal infections and complications of birth), the formal diagnostic symptoms and signs of schizophrenia are not typically manifested until late adolescence or early adulthood. The emergence of these pathologies at this critical period suggests a relationship between these disorders and reproductive hormones.

During late adolescence and early adulthood, the brain undergoes extensive synaptic remodeling, including reduction in dendritic arborization, axon myelination and synaptic pruning. The integrity of these processes may be crucial for maturation of a wide range of sensory and cognitive functions that are impaired in schizophrenia.

In the recent years, several studies have uncovered the critical role of GPR54, a G protein-coupled receptor sometimes named AXOR12 or SNORF11, and kisspeptin, the natural ligand for GPR54, in the control of pubertal development (de Roux et al., 2003; Seminara et al., 2003).

Agonists of the SNORF11 receptor, such as KISS-1 peptide fragments, have been characterized as cancer metastasis suppressors (Ohtaki et al, 2001) and as analgesics (WO 2003/003983). US 2002/0106766 discloses the rat AXOR12 gene sequence, methods for identifying agonists and antagonists/inhibitors and potential uses thereof. WO 2004/087622 discloses GPR54 receptor agonist and antagonist useful for the treatment of gonadotropin related diseases.

Kisspeptin, the primary translation product of the gene KiSS-1, is a G-protein coupled receptor ligand for GPR54. KiSS-1 was originally identified as a human metastasis suppressor gene that has the ability to suppress melanoma and breast cancer metastasis (Lee et al., 1996). A polymorphism in the terminal exon of this mRNA results in two protein isoforms. An adenosine present at the polymorphic site represents the third position in a stop codon. When the adenosine is absent, a downstream stop codon is utilized and the encoded protein extends for an additional seven amino acid residues.

The primary translation product of KiSS-1 is a 145 amino acid polypeptide (Kp-145). C-terminal amidated peptides of kisspeptin have been disclosed in U.S. Pat. Nos. 6,699,965 and 7,314,754: Kp-54, also known as metastin, containing 54-amino acid residues from positions 68 (Gly) to 121 (Phe) of Kp-145, and the shorter peptides Kp-10 (residues 112-121), Kp-13 (residues109-121) and Kp-14 (residues109-121). The peptides are disclosed as suppressors of tumor metastasis and as playing an important role in the placenta. Kp-10 was later found to be a physiological invasion inhibitor of primary human trophoblasts (Bilban et al., 2003). Kisspeptin was shown to elicit the release of gonadotropin, through the stimulation of gonadotropin-releasing hormone (GnRH) secretion, by direct activation of preoptic GnRH neurons. During transition from juvenile to adulthood, there is an increase in expression of KiSS-1 mRNA in the anteroventral periventricular nucleus, which is believed to regulate GnRH neurons. Furthermore kisspeptin and GPR54 are expressed in the dentate gyrus of the hippocampus and were shown to regulate synaptic plasticity and BDNF levels (Arai, 2008). Kisspeptin has been further described as an endogenous factor which is dynamically regulated by neuronal activity and may play a role in cognition and in the pathogenesis of epilepsy (Arai et al., 2009).

SUMMARY OF THE INVENTION

The present invention relates, in one aspect, to a GPR54 agonist or antagonist for treatment of a disease or disorder presenting behavioral abnormalities associated with impairment of sensory gating function, and/or for treatment of depression, and/or for improving cognitive function. In certain preferred embodiments, the disease or disorder presenting behavioral abnormalities associated with impairment of sensory gating function is schizophrenia; in other embodiments, said disease or disorder is Huntington's chorea, obsessive-compulsive disorder (OCD), attention deficit hyperactivity disorder (ADHD), or Tourette's syndrome.

In certain embodiments, the invention provides a GPR54 agonist for the above-defined purposes, wherein said GPR54 agonist is selected from:
(i) kisspeptin of the amino acid sequence set forth in SEQ ID NO:1;
(ii) an isoform of kisspeptin;
(iii) a recombinant form of kisspeptin;
(iv) a kisspeptin peptide of a sequence comprised within the amino acid sequence set forth in SEQ ID NO:1;
(v) an analog of said kisspeptin peptide of (iv); and
(vi) a salt or chemical derivative of said kisspeptin peptide of (iv) or analog of (v).

In certain embodiments, the GPR54 agonist for use in the present invention is kisspeptin of the sequence set forth in SEQ ID NO: 1, including 145 amino acids, in either one of its natural isoforms or recombinant forms.

In other embodiments, the GPR54 agonist is a kisspeptin peptide, a salt or a chemical derivative thereof. As used herein, the term "kisspeptin peptide" refers to a synthetic peptide derived from kisspeptin, namely, a peptide which sequence is comprised within the 145-amino acid sequence of kisspeptin of SEQ ID NO: 1. The term "chemical derivative" refers to a chemical derivatization at the N-terminal, C-terminal or at a free functional group, e.g., hydroxyl, amino or carboxy group, of an amino acid residue of the peptide, and is preferably an ester, more preferably an amide, of the carboxy terminal group of the peptide.

In certain embodiments, the kisspeptin peptide is the 54-peptide comprising the amino acid residues 68-121 of kisspeptin and designated metastin, KiSS-1 (68-121) or Kp-54, preferably in the amide form of the sequence set forth in SEQ ID NO:2. Short peptides derived from metastin may be characterized by the numbering of the amino acid residues of the whole kisspeptin (SEQ ID NO:1) or of the metastin (SEQ ID NO:2) identified as residues 1-54. Examples of such short metastin peptides include the decapeptide Kp-10 amide (SEQ ID NO:3), also identified as KiSS-1 (112-121) or metastin (45-54); Kp-13 amide (SEQ ID NO:4), also identified as KiSS-1 (109-121) or metastin (42-54); and Kp-14 amide (SEQ ID NO:5), also identified as KiSS-1 (108-121) or metastin (41-54). Additional examples of kisspeptin peptides for use in the present invention include, but are not limited to, KiSS-1 (93-122) (SEQ ID NO: 6), KiSS-1 (106-122) (SEQ ID NO: 7), KiSS-1 (94-122) (SEQ ID NO: 8), KiSS-1 (107-122) (SEQ ID NO: 9), and KiSS-1 (114-122) (SEQ ID NO: 10). It is to be understood that in accordance with the present invention, the peptides designated herein KiSS-1 (X-122) encompass also the peptides KISS (X-121), and vice-versa, and the amides thereof.

In more preferred embodiments, the kisspeptin peptide for use in the present invention is the decapeptide known as Kp-10 that has the amino acid sequence YNWNSFGLRF—$NH_2$ (SEQ ID NO: 3). This decapeptide will be referred to herein in the application as "Kp-10" or as "Kp-10 (SEQ ID NO:3)".

In certain embodiments, the GPR54 agonist is a kisspeptin peptide analog, in which one or more of the amino acid residues have been deleted or replaced by the corresponding D-isomer or by a natural or a non-natural amino acid residue.

For replacement, any of the natural amino acids may be used such as alanine or a natural amino acid that preferably has a similar structure or charge of the amino acid to be replaced, for example, an aromatic amino acid such as phenylalanine, tyrosine, tryptophan or histidine can be replaced by another of the aromatic amino acids, a positively charged amino acid such as lysine can be replaced by arginine and vice-versa, a negatively charged amino acid such as glutamic acid can be replaced by aspartic acid and vice-versa, a hydrophobic amino acid such as leucine can be replaced by isoleucine and vice-versa, and the like. Examples of the decapeptide of SEQ ID NO: 3 analogs in which one of the amino acid residues is replaced by alanine are the peptides of SEQ ID NO: 11 to SEQ ID NO: 20, all in the form of amides. Examples of the peptide of SEQ ID NO:3 analogs in which one of the amino acids was replaced by a structurally similar amino acid residue are the peptides of SEQ ID NO: 21 (Y at position 1 replaced by F); SEQ ID NO: 22 (N at position 2 replaced by D); SEQ ID NO: 23 (N at position 4 replaced by D); SEQ ID NO: 24 (S at position 5 replaced by T); SEQ ID NO: 25 (F at position 6 replaced by Y); SEQ ID NO: 26 (L at position 8 replaced by I); SEQ ID NO: 27 (R at position 9 replaced by K); and SEQ ID NO: 28 (F at position 10 replaced by H), all in the form of amides.

Also contemplated by the invention are analogs in which an amino acid residue of the kisspeptin peptide is replaced by the corresponding D-amino acid residue. Examples are the analogs of the peptide of SEQ ID NO:3 of the sequences SEQ ID NO:29 (dY at position 1); SEQ ID NO:30 (dF at position 6); and SEQ ID NO:31 (dF at position 10) (Curtis et al., 2010).

Analogs can also be obtained by replacement of one of the amino acid residues by a non-natural amino acid such as, but not limited to, Nα-methyl amino acids, Cα-methyl amino acids, β-methyl amino acids, β-alanine (β-Ala), norvaline (Nva), norleucine (Nle), 4-aminobutyric acid (γ-Abu), 2-aminoisobutyric acid (Aib), ornithine (Orn), hydroxyproline (Hyp), 4-(aminomethyl)benzoic acid (Amb), 2-amino-3-(naphth-2-yl) propanoic acid (Nal), sarcosine, citrulline, cysteic acid, and cyclohexylalanine. Examples are the analogs of short peptides comprised within the sequence of the peptide of SEQ ID NO:3 of the sequences Bis(Py)-Amb-Phe-Gly-Leu-Arg-Trp-$NH_2$ (SEQ ID NO: 32), Gu-Amb-Phe-Gly-Leu-Arg-Trp-$NH_2$ (SEQ ID NO: 33), Ac-Trp-Asn-Arg-Phe-Gly-Leu-Arg-Trp-$NH_2$ (SEQ ID NO: 34) (Niida et al., 2006), and H-Amb-Nal(2)-Gly-Leu-Arg-Trp-$NH_2$ (SEQ ID NO: 35), wherein Gu is 1-methyl-guanidine, Ac is acetyl (Tomita et al., 2006).

GPR54 antagonists for use in the present invention can be screened as described in WO 2004/087622 and include, but are not limited to, compounds able to inhibit the activation of GPR54 including compounds capable of interacting with natural agonists of GPR54, such as kiss-1 peptide, to inhibit the binding of said agonists, or to inhibit the activation of GPR54 resulting from said binding. GPR54 antagonists also include inhibitors of the expression of GPR54 such as for instance antisense oligonucleotides, or interfering RNAsi, or ribozymes, targeting the GPR54 gene.

In certain embodiments, the kisspeptin peptide amide of SEQ ID NO:3 is for use in treating schizophrenia by ameliorating the psychotic and depression symptoms and the cognitve impairment associated with schizophrenia. In other embodiments, the kisspeptin peptide amide of SEQ ID NO:3 is for use as anti-psychotic, anti-depressant or for improvement of cognitive functions in non-schizophrenic patients.

In another aspect, the invention relates to a pharmaceutical composition comprising a GPR54 agonist or antagonist and a pharmaceutically acceptable carrier, for treatment of a disease or disorder presenting behavioral abnormalities associated with impairment of sensory gating function, and/or for treatment of depression, and/or for improving cognitive function.

In a further aspect, the present invention provides a method for treatment of a disease or disorder presenting behavioral abnormalities associated with impairment of sensory gating function, and/or for treatment of depression, and/or for improving cognitive function, which comprises administering to a patient in need thereof an effective amount of a GPR54 agonist or antagonist.

In yet another aspect, the present invention provides a method for the treatment of schizophrenia by ameliorating/alleviating the psychotic and/or depression symptoms and the cognitve impairment associated with schizophrenia, which comprises administering to a patient in need thereof an effective amount of a peptide of the sequence set forth in SEQ ID NO: 3, optionally in combination with one or more drugs used for treatment of schizophrenia.

It is also contemplated by the invention to determine the susceptibility of an individual at the puberty stage to develop schizophrenia at adulthood by measuring the level of Kiss-1 expression in said individual at puberty. An impaired/abnormal level of expression of the gene Kiss-1 at puberty indicates an abnormal sensorimotor gating and the susceptibility of developing the disease at adulthood. In this case, administration of Kisspeptin or a kisspeptin peptide, preferably, the peptide of SEQ ID NO:3, at the critical stages of puberty/adolescence, would prevent the onset of schizophrenia, or at least prevent the development of psychotic symptoms, at adulthood.

BRIEF DESCRIPTION OF DRAWINGS

FIGS. 7A-7B show therapeutic effect of Kp-10 in a mouse model for schizophrenia.

(7A) PPI in offspring of PBS treated dams (n=11) compared to PPI of offspring of poly I:C treated dams that were treated with Kp-10 (n=18) or PBS (n=18) at 8 weeks of age (Repeated measure ANOVA, F $(2,41)=8.2$, $P=0.01$; *$P<0.05$, Fisher LSD post hoc analysis). (7B) PPI in adult naive mice that were treated with Kp-10 (n=9) or PBS (n=9) at 8 weeks of age (Repeated measure ANOVA, F (1,16)=0.001, P=0.9). Representative data from prepulse of 73 are presented.

FIGS. 8A-8B show that Kp-10 injections improve PPI in mouse models for schizophrenia. (8A) PPI in adult offspring of saline treated dams (n=7) compared to PPI of offspring of poly I:C treated dams that were treated with Kp-10 (n=8) or PBS (n=10) 30 min before PPI analysis (Repeated measure ANOVA, F (2,22)=4.6, P=0.02; *P<0.05, Fisher LSD post hoc analysis). (8B) PPI in wild type mice (n=7) was tested and compared to that of mice after treatment with Kp-10 (n=6) and/or MK-801(n=6). (Repeated measure ANOVA, F (2,16)=5.72, P=0.01; *P<0.05, Fisher LSD post hoc analysis).

FIGS. 9A-9E show that single and repeated Kp-10 injections improve behavior performance in naïve mice. (9A) PPI in male C57B1/6J naïve mice (n=8) was compared to that of mice that were injected with 100 μl of 1/10/100 μM Kp-10 (n=9/15/12) (Repeated measure ANOVA, F (3,40)=3.9, P=0.01; *P<0.05, Fisher LSD post hoc analysis). (9B) PPI in female C57B1/6J naïve mice (n=8) was compared to that of mice that were injected with Kp-10 (n=8) (Repeated measure ANOVA, F (1,14)=8.1, P=0.01; *P<0.05, Fisher cLSD post hoc analysis). (9C) Repeated PPI measurement of the male mice which received 100 μl of 100 μM Kp-10, 24 h after treatment (Repeated measure ANOVA, F (1,14)=0.02, P=0.8). (9D) Repeated Kp-10 (n=13) injections 24 h after the first injection improved PPI compared to the PBS treated mice (n=10). (Repeated measure ANOVA, F (1,21)=9.6, P=0.005; *P<0.05, Fisher LSD post hoc analysis). (9E) Repeated Kp-10 injections (n=15) 7 days after the first injection improved PPI compared to the PBS-treated mice (n=10). (Repeated measure ANOVA, F (1,23)=8.3, P=0.008; *P<0.05, Fisher LSD post hoc analysis). Representative data from prepulse of 73 are presented.

Figure 10A:
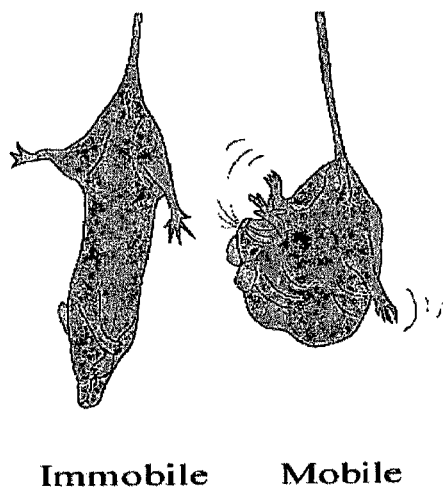
Figure 10B:
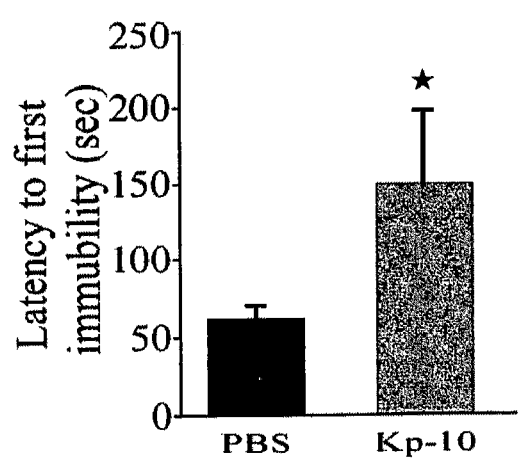
Figure 10C:
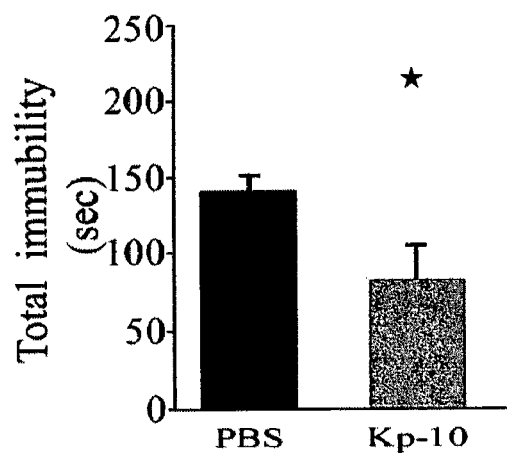

FIGS. 10A-10C show that Kp-10 improves behavior performance. (10A) Scheme showing the tail suspension test (10B) Kp-10 prolonged the latency of the first immobility in the tail suspension test compared to PBS (Student's t test P=0.006). (10C) Kp-10 reduces the total immobility time in the tail suspension test compared to PBS (Student's t test P=0.03).

Figure 11A:
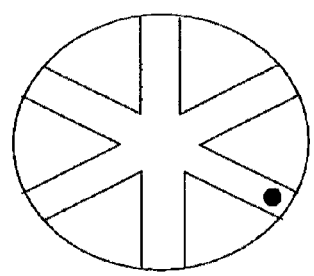
Figure 11B:
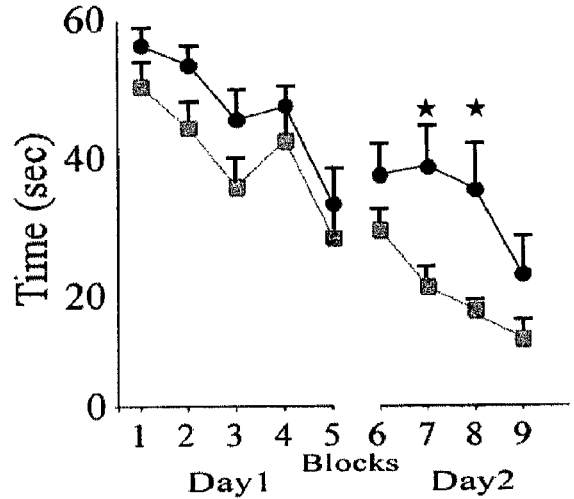
Figure 11C:
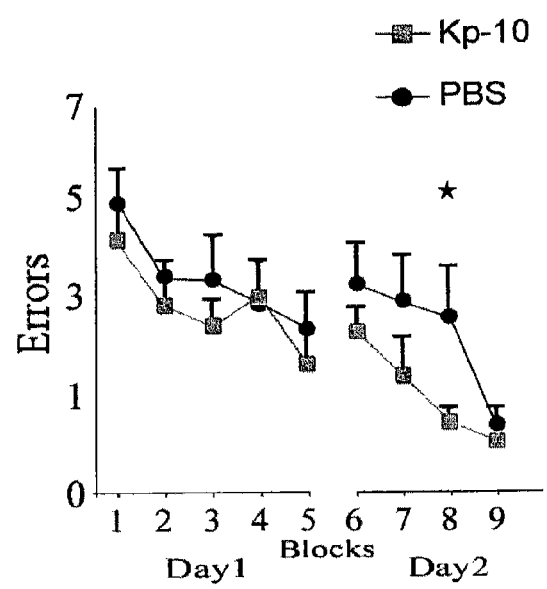

FIGS. 11A-11C show the performance of mice in the radial arm water maze (RAWM). (11A) Scheme showing the radial arm water maze (RAWM). Kp-10 injection (n=8) improve the time (11B) and reduce the number of errors (11C) (Repeated measure ANOVA, F (1,14)=6.0, P=0.02; *P<0.05, Fisher LSD post hoc analysis) in the way of SCID mice to the platform, compared to the PBS treated group (n=8).

Figure 12A:
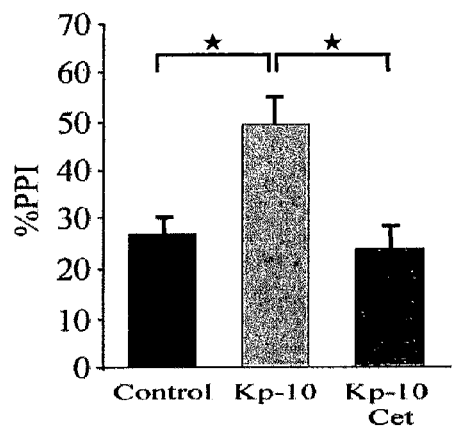
Figure 12B:
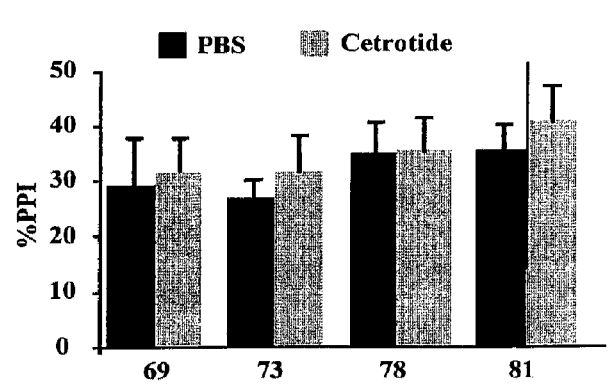
Figure 12C:
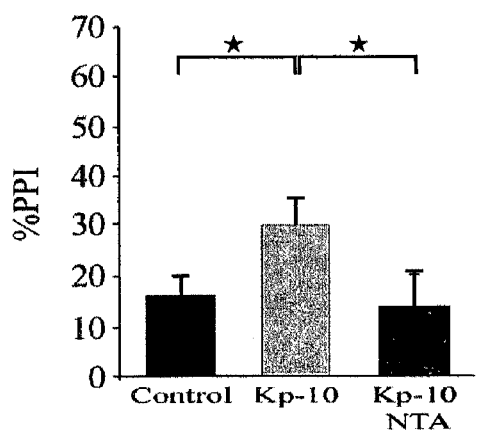

FIGS. 12A-12C show that neurotensin and GnRH antagonist abolish the effect of Kp-10 on PPI. (12A) PPI in C57B1/6J mice (n=10) was tested and compared to that in C57B1/6J mice after treatment with Kp-10 (n=7) and/or GnRH antagonist, Cetrotide™ (n=10). (Repeated measure ANOVA, F (2,24)=8.7, P=0.001; *P<0.05, Fisher LSD post hoc analysis). (12B) PPI in C57B1/6J mice (n=10) was tested and compared to that in C57B1/6J mice after treatment with the GnRH antagonist Cetrotide™ alone (n=10). (Repeated measure ANOVA, F (1,18)=0.05, P=0.8). Representative data from prepulse of 73 are presented. (12C) PPI was tested in C57B1/6J mice (n=12) and compared to that after treatment with Kp-10 (n=13) and/or neurotensin antagonist NTA (n=12). (Repeated measure ANOVA, F (2,34)=3.8, P=0.03; *P<0.05, Fisher LSD post hoc analysis).

DETAILED DESCRIPTION OF THE INVENTION

Neuropsychological syndromes including schizophrenia often do not manifest until late adolescence or early adulthood. Studies attributing a role in brain maintenance to the immune system led us to propose that immune malfunction underlies the late onset of such diseases/syndromes, due to immune-dependent regulation of those brain functions that normally develop at adolescence. One such function is sensorimotor gating, the ability to segregate a continuous stream of sensory and cognitive information, and to selectively allocate attention to a significant event by silencing the background; this activity is impaired in schizophrenia, as well as in several other neurodegenerative and psychiatric diseases such as, Huntington's chorea, obsessive-compulsive disorder (OCD), attention deficit hyperactivity disorder (ADHD), and Tourette's syndrome.

Recently, we and others showed that the adaptive immune system, and specifically the population of T-cells recognizing central nervous system (CNS) antigens, has a key role in CNS maintenance under physiological conditions (Kipnis et al., 2004; Ziv et al., 2006). Furthermore, we demonstrated that vaccination with a CNS-like peptide can counteract the schizophrenia-like behavioral malfunctions induced in mice by MK-801 or amphetamine (Kipnis et al., 2004). Taken together with the decreased immune response to brain antigens (Kipnis et al., 2006), and the vast evidence of immune dysfunction in schizophrenic patients (Rothermundt et al., 2001), these findings led us to propose that the congenital risk factors that correlate with schizophrenia result in immunological malfunction later in life. Such immunological malfunction could lead to the onset of various abnormal behaviors such as sensorimotor gating deficit, at the critical ages of adolescence and early adulthood.

Among the critical environmental factors that have been linked to an increased risk of developing schizophrenia later in life are maternal infections during pregnancy. Since the specificity of the viral infection appears irrelevant to schizophrenia development, administration of the viral mimetic, polyriboinosinic-polyribocytidylic acid (poly I:C), during pregnancy, causing non-specific immune activation, is accepted as a valid animal model for inducing this disease. In addition, some of the symptoms observed in human patients were also seen in this animal model, including a sensorimotor gating deficit, one of the hallmark symptoms of schizophrenia (Swerdlow et al., 2006), and alterations in limbic morphology (Zuckerman et al., 2003). Moreover, in this model, similarly to the human disease, the psychopathological behavioral symptoms such as abnormal prepulse inhibition (PPI) develop only at adulthood (Zuckerman et al., 2003). The exact mechanism through which poly I:C acts to increase the risk for these neurodevelopmental pathologies is not fully understood. However, the maternal cytokine response to infections is suspected to have a crucial role in this association. One possible outcome of such a cytokine response is the abnormal development of the immune system of the progeny. Indeed, in schizophrenic patients, several immune abnormalities have been described, including a shift in the cytokine response. In addition, in some schizophrenic patients, a reduced immune response to brain antigens was observed (Kipnis et al., 2006).

In accordance with the present invention, using rat and mouse models of congenital schizophrenia induced by prenatal immune challenge with poly I:C, in which abnormal sensorimotor gating has a delayed appearance, we demonstrate herein a form of immune deficit in the adult offspring shown by a specific reduction in the T cell response to CNS antigens, despite an elevation in non-specific T-cell proliferation (Example 1). We demonstrated in this neurodevelopmental animal model for schizophrenia that immune activation during pregnancy causes a form of immune deficit in the offspring, indicating a novel functional linkage between maternal infection, abnormal cellular immunity, and delayed onset of schizophrenia-like behavior. The fact that EAE (experimental autoimmune encephalomyelitis) could be induced in the progeny of poly I:C treated rats, though their disease was milder, indicates that maternal infection does not eliminate CNS-specific lymphocytes, but alters their regulation.

We further showed that similarly to the poly I:C mice and rats, in congenitally immune-deficient mice (SCID), as well, abnormal sensorimotor gating function measured as PPI developed only at adulthood and could be reversed by immune reconstitution, i.e., transfer of lymphocytes from wild-type mice (Example 2). Whether the decreased immune response to brain antigens is the cause of the disease or its outcome is not yet known. Here, we show that congenital immune deficits resulting in abnormal PPI are manifested only in adulthood, and that transfer of lymphocytes from wild-type mice can prevent and/or restore this dysfunction. These data indicate that the abnormal sensorimotor gating, as tested by PPI, could be attributed, at least in part, to a defect in adaptive immunity. The fact that transfer of lymphocytes to adult SCID mice was sufficient to reverse the abnormal PPI indicates that such behavioral abnormalities are not solely the result of abnormal brain development or pathology, but rather reflect functional deficits in the continuous contribution of peripheral immunity to brain maintenance. Although SCID mice were reconstituted with the total lymph-node cell population, we attribute the beneficial effect of immune reconstitution on behavior to the adaptive immune cells, and specifically to T-lymphocytes; the other immune cell populations in SCID mice are normal.

In addition, we showed that adolescence and early adulthood is a period during which the adaptive immune system modulates developmental processes in the brain such as hippocampal neurogenesis (Example 3) and KiSS-1 expression (Example 4). In these examples, it is shown that hippocampal neurogenesis and expression of KiSS-1, a gene that is considered the gatekeeper for the onset of puberty (de Roux et al., 2003; Seminara et al., 2003) and regulates hippocampal synaptic transmission (Arai, 2008; Arai et al., 2005), is elevated at adolescence, and that this is an immune-dependent event. Further, we show that kisspeptin is involved in regulating sensorimotor gating and administration of kisspeptin to congenitally immune deficient mice is shown to restore their normal behavior as measured by PPI (Example 4). Together, hippocampal neurogenesis and KiSS-1 mRNA expression indicate an immune-related mechanism which may underlie the late onset of behavioral malfunctions characteristic of schizophrenia.

In accordance with the present invention, we show that administration of kisspeptin at adolescence prevents psychotic-like symptoms at adulthood in the poly I:C model for schizophrenia. A single injection of Kp-10 (SEQ ID NO:3) at adolescence was able to prevent the onset of symptoms of schizophrenic behavior at adulthood as measured by PPI (Example 5). We have further demonstrated that kisspeptin is involved in regulation of hippocampal brain-derived neurotrophic factor (BDNF) levels. BDNF has important functions in the development of the nervous system and in brain plasticity-related processes such as memory, learning, and drug addiction. Various studies have shown possible links between BDNF and conditions such as depression, schizophrenia, obsessive-compulsive disorder, Alzheimer's disease, Huntington's disease, Rett syndrome, and dementia, as well as anorexia nervosa and bulimia nervosa.

We have further demonstrated that Kp-10 was able to reverse psychotic-like symptoms in two different animal models of schizophrenia (poly I:C model and administration of the NMDA antagonist MK-801) after the onset of the disease symptoms (Example 6). Further, Kp-10 was found to improve behavior performance in naïve mice (Example 7).

In accordance with the present invention we show that Kp-10 improves psychotic-like behavior. Both the therapeutic ability of Kp-10 to prevent symptoms onset and its ability to cure ongoing symptoms demonstrate the anti-psychotic ability of Kp-10, however, it is clear that the mechanism of action in each case is different. As a prophylactic agent, Kp-10 affects long lasting developmental processes, while the therapeutic effect of Kp-10 most likely involves rapid and acute changes in plasticity.

Importantly, PPI deficits are not unique to a single form of psychopathology. Impairment of PPI has been reported in several other diseases such as autistic disorder (AD), Huntington's chorea, obsessive-compulsive disorder, attention deficit hyperactivity disorder (ADHD), and Tourette's syndrome. Therefore, PPI is often used as a paradigm, for assessing the modulation of early information processing and is widely used to investigate antipsychotic drug action in animals.

To evaluate whether Kp-10 also possesses an antidepressive effect we used the tail suspension test. We found that Kp-10 significantly increased the latency to the first immobility and reduced the duration of the total immobility, suggesting an antidepressive effect of Kp-10 (Example 8). In addition, Kp-10 was also found to improve the performance in spatial learning and memory test (Example 9).

Further, neurotensin and GnRH antagonists were able to abolish the effect of Kp-10 (SEQ ID NO:3) on PPI, indicating that Kp-10 mediates its activities in a neurotensin and GnRH dependent manner (Example 10).

In summary, we found that in naïve animals hippocampal expression of KiSS-1 is elevated at adolescence and that KiSS-1 expression at puberty was impaired in both SCID mice and in adult offspring of poly I:C treated dams. Moreover, exogenous administration of a kisspeptin-derived peptide partially reversed the gating deficits in the SCID mice and also in adult offspring of poly I:C treated dams. Our results indicate that a form of congenital immune deficiency may be a key factor that determines manifestation of developmental neuropathology with onset only at early adulthood.

In the present invention, we identified kisspeptin as a novel immune regulated player in hippocampal plasticity. KiSS-1 and its receptor are expressed in the dentate gyrus of the hippocampus and can regulate synaptic plasticity (Arai, 2008; Arai et al., 2005) and BDNF levels (Arai et al., 2009). Kisspeptin was originally identified as a key signaling factor in the neural control of fertility (de Roux et al., 2003). It was shown to elicit the release of gonadotropin, through the stimulation of gonadotropin-releasing hormone (GnRH) secretion, by direct activation of preoptic GnRH neurons. During the transition from juvenile to adulthood, there is an increase in the expression of KiSS-1 mRNA in the anteroventral periventricular nucleus, which is believed to regulate GnRH neurons. Here, we describe a similar increase in expression of KiSS-1 mRNA in the hippocampus of wild-type mice in adolescence, indicating its involvement in regulating hippocampal plasticity at this critical age. Such an elevation in KiSS-1 expression was absent in SCID mice, but was reestablished following immune reconstitution. In addition, we found reduced levels of KiSS-1 mRNA in the hippocampus of adult poly I:C affected offspring. It is important to note that in order to reduce the effect of sex hormonal fluctuations these experiments were done using male mice.

Nevertheless, the present findings propose a novel approach for uncovering the mystery of gender differences in psychotic diseases.

In addition, we demonstrated the causal relation between reduced KiSS-1 expression and the abnormal behavior in SCID mice. Injection of Kp-10 (SEQ ID NO:3), previously shown to activate GPR54 in vivo (Gottsch et al., 2004), restored PPI in SCID mice to normal (Example 4). Taken together, these results show that an absent or abnormal immune response to CNS antigens can lead to the late onset of schizophrenia-like symptoms, though the precipitating event occurred prenatally.

In accordance with the present invention, our results further indicate that exogenous administration of kisspeptin or an active peptide derived from it, namely Kp-10, in puberty, might prevent the onset of psychotic symptoms or improve them after disease onset. We showed that in a neurodevelopmental mouse model for schizophrenia, Kp-10 (SEQ ID NO:3) given at adolescence prevented onset of psychotic symptoms at adulthood. In addition, we found that the peptide had antipsychotic effects in a pharmacological animal model for schizophrenic behavior, improved cognitive performance and reversed behavioral despair in naive mice.

The effects of Kp-10 were mediated, at least in part, through neurotensin, a known endogenous antipsychotic neuropeptide and through a GnRH dependent pathway. Our results according to the present invention identified a novel mental and cognitive role for kisspeptin that are unrelated to schizophrenia. In addition, due to the fact that impairment of PPI was attributed to several other mental disorders including autistic disorder (AD), Tourette's syndrome, and attention deficit hyperactivity disorder (ADHD), kisspeptin and the peptides thereof may also be used in treating these disorders.

Kisspeptin is a peptide with a diverse and multifunctional nature, involving varied whole body physiological systems and acting at all levels of the reproductive axis. Other functions of kisspeptin include a role in the control of insulin and/or glucagon secretion, local control of ovulation, and blocking ectopic implantation. The results we presented here point to a role of kisspeptin in regulation of cognitive and mental behavior. The regulation of Kiss-1 expression at least in the hippocampus is immune dependent. Our findings imply that kisspeptin may lie in the important intersection of immune-metabolism and immune-reproduction with or without further connection to cognition. In addition, the immune effect on cognition is frequently mediated by insulin-like growth factor-1 (IGF-1).

In preferred embodiments of the invention, kisspeptin peptides and analogs thereof as defined herein are disclosed as useful for treatment of schizophrenia and other diseases presenting behavioral abnormalities associated with impairment of sensory gating function as well as for treatment of psychotic symptoms, depression symptoms and improvement of cognitive functions both in schizophrenic and non-schizophrenic patients. In preferred embodiments, the kisspeptide peptin is Kp-10 of SEQ ID NO:3.

As used herein, the term "treatment" includes ameliorating, alleviating, attenuating and/or even abolishing symptoms associated with the disease or disorder. In case of schizophrenia, it is contemplated by the invention that the treatment with the kisspeptin or a peptide thereof, preferably the peptide Kp-10 of SEQ ID NO:3, will ameliorate/alleviate the psychotic and/or depression symptoms associated with the disease and/or will improve the cognitive functions impaired in the schizophrenic patient.

The peptide of SEQ ID NO:3, may be administered as a sole medicament or in combination with other suitable drugs used in the treatment of schizophrenia such as, but not limited to clozapine, amisulpride, olanzapine, risperidone, quetiapine, ziprasidone, aripiprazole or paliperidone.

The peptides used in the present invention are commercially available or may be synthesized by methods well known in the art such as the F-moc solid phase peptide synthesis technique.

The kisspeptin peptide for use in the invention may be in its free form or in the form of a salt or a chemical derivative thereof such as an ester or an amide, more preferably an amide of the carboxy terminal group. As used herein, the term "salts" refers to both salts of carboxyl groups and to acid addition salts of amino groups of the peptide molecule. Salts of a carboxyl group, may be formed by means known in the art and include salts with inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. The esters may be formed by reacting suitable alcohols used in peptide chemistry with terminal carboxyl groups or with free non-terminal carboxyl groups of aspartic or glutamic acid residues.

For use in the present invention, the GPR54 agonists or antagonist can be formulated into pharmaceutical compositions with a pharmaceutically acceptable carrier by methods well known in the art. The protein or peptide can be mixed with physiologically acceptable known carriers and further excipients such as stabilizers, flavoring agents, antiseptics, binders, antioxidants, etc and formulated for administration by any suitable route.

Any suitable composition and route of administration is encompassed by the invention, including oral (in the form of tablets, capsules, microcapsules, and the like), parenteral (e.g., in the form of subcutaneous, intramuscular, intraarticular, or intravenous injection), inhalation, intranasal (in the form of sprays), intrathecal, intraperitoneal, intradermal, transdermal or other known routes of administration suitable for the administration of peptides to human beings.

The dose of the peptide to be administered will be determined by the competent physician and will depend on the agent used, the severity of the disease, the age, and the weight of the patient, and may vary from 0.1-100 mg, preferably 1.0-50 mg, more preferably 1.0-20 mg for oral application; or from 0.01-30 mg, preferably 1.0-30 mg, more preferably 1.0-20 mg for parenteral application; or from 0.01-10 mg, preferably 0.05-5 mg, more preferably 0.05-0.2 mg for intravenous (IV) application.

The invention will now be illustrated by the following non-limiting Examples.

EXAMPLES

Materials and Methods

Animals. Inbred wild-type and Prkdc$^{scid}$ (SCID) mice on BALB/c/OLA, or C57B1/6 backgrounds, and inbred Lewis rats were supplied by the Animal Breeding Center of the Weizmann Institute of Science. SCID (severe combined immunodeficiency) mice lack both T- and B-cell populations due to a mutation on Chromosome 16 responsible for deficient Prkdc activity (protein kinase, DNA activated, catalytic polypeptide). This mutation leads to defect in the rearrangement of genes that code for antigen-specific receptors on lymphocytes. However, they have a normal hematopoietic microenvironment, and normal antigen-presenting cell, myeloid, and NK cell functions. Animals were matched for age in each experiment: adult animals (12-18 weeks old) were used in all the experiments, unless described otherwise, and the ages at which the animals were used are indicated for each relevant experiment. Male mice and female rats were used in all experiments. All animals were handled according to the regulations formulated by the Weizmann Institute's Animal Care and Use Committee and maintained in a pathogen free environment.

Poly I:C administration. Rats or mice were bred, and the first day after copulation was defined as day 1 of pregnancy. On gestation day 15, pregnant animals were injected intravenously with 4.0 mg/kg poly I:C (Sigma-Aldrich, Israel) dissolved in saline, or an equivalent volume of saline as a control. Both rats and mice received the same protocol of poly I:C administration.

Figure 1A:
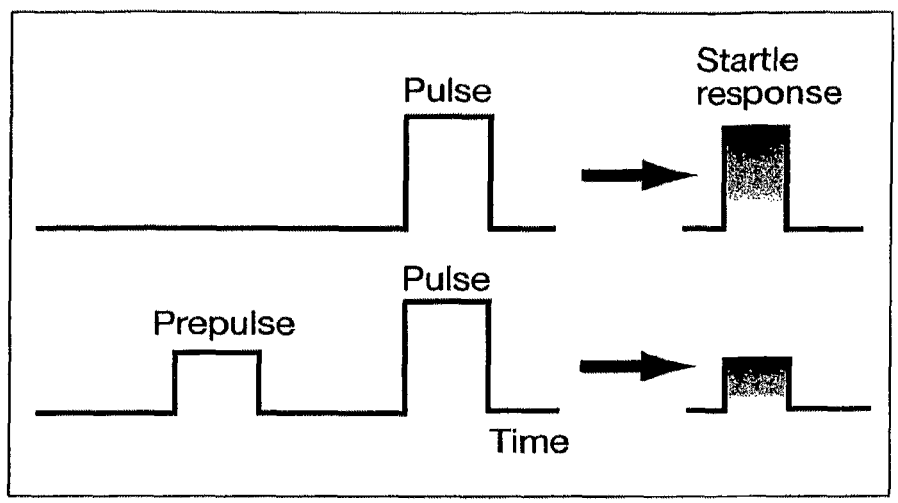
FIGS. 1A-1B show that immune activation with poly I:C during pregnancy causes abnormal PPI in the offspring of Lewis rats. (1A) Scheme showing principles of PPI measurements. (1B) PPI in the offspring of the poly I:C-treated Lewis rats was reduced compared to PPI in the offspring of saline-treated dams (n=7) (Repeated measure ANOVA: groups: $F(1,12)=4.85$, $P=0.04$; prepulse intensities: $F(3,36)=5.68$, $P=0.003$; groups x prepulse intensities: $F(3,36)=0.50$; $P=0.68$. One-way ANOVA: 69 dB: $F(1,12)=1.95$, $P=0.19$; 73 dB: $F(1,12)=10.06$, $P=0.008$; 78 dB: $F(1,12)=8.89$, $P=0.01$; 81 dB: $F(1,12)=1.70$, $P=0.22$; *$P<0.05$, Fisher LSD post hoc analysis). Values represent means±S.E.M.

Prepulse Inhibition (PPI). PPI testing was performed within startle chambers purchased from Med Associates Inc (Med Associates, St. Albans, Vt., USA). PPI was analyzed as described previously (Kipnis et al., 2004). Briefly, during a period of acclimation, a 65-dB background noise was applied for 5-min, and continued throughout the test session. All sessions for testing of PPI consisted of startle trials (pulse alone, 40-ms, 120-dB), prepulse trials (prepulse 20-ms, 69, 73, 78, or 81 dB followed by a (100-ms delay) pulse), and no-stimulus trials. All sessions were presented in pseudo-random order. The average time between trials was 15 s (range 12-30 s). PPI was calculated as: % PPI=100−{[(startle response for prepulse+pulse)/(startle response for pulse-alone)]×100}. In all the experiments, there were no significant differences between groups in trials of startle reactivity to pulse alone, and in no-stimulation trials. Data from no-stimulation trials are not included in the results because the values obtained were negligible relative to values from trials containing startle stimuli. Reduced PPI is associated with schizophrenia-related behavior. The same protocol was used in mice and rats (FIG. 1A).

Tail suspension test. The tail suspension apparatus was made of horizontal metal rod supported by a stand. Each mouse was suspended from its tail using adhesive tape, suspending each mouse individually. The immobility time was measured during a 6 min observation period, latency to first immobility and total immobility was calculated (FIG. 10A).

Radial arm water maze (RAWM). Mice were tested for two days on 6 radial arm water maze paradigm in a water pool, as described in Alamed et al. (2006). Briefly, mice received Kp-10 injection in the beginning of each day. On the first day, 15 trials were performed, in trials 1, 3, 5, 7, 9 and 11 the platform was visible, and in all other trials the platform was hidden. On the second day, 12 trials were performed, all of them with hidden platform. The time required to reach the platform and the number of errors (incorrect arm entries) in 1-min time period were recorded (FIG. 11A).

Vaccination. Adult rats were immunized at the base of the tail with 75 µg of the peptide $MBP_{68-86}$ (SEQ ID NO: 36) (synthesized at the Weizmann Institute of Science), emulsified in an equal volume of complete Freund's adjuvant (CFA; Difco, Detroit, Mich.) containing 5 mg/mL Mycobacterium tuberculosis (strain H37Ra, BD Diagnostics).

Proliferation assay. Peripheral lymph nodes were harvested and mashed. The proliferation assay was done as described previously (Hauben et al., 2003). Briefly, lymphocytes were cultured in 200 µl of medium ($1.5×10^6$ cells/ml) with ovalbumin (Ova 10 µg/ml, Sigma-Aldrich), $MBP_{68-86}$ (10 µg/ml, Weizmann Institute of Science), concanavalin A (Con A; 1.25 µg/ml Sigma-Aldrich) or without antigen, for 72 hr. [$^3$H] Thymidine (0.2 µCi/well) was added during the last 18 h of culture. Cells were harvested, and incorporation of [$^3$H] thymidine was measured using a direct γ-counter. The proliferation index (PI) was calculated as the ratio between the proliferation in the presence of antigen versus proliferation in the absence of antigen.

EAE. To induce experimental autoimmune encephalomyelitis (EAE), adult female Lewis rats were immunized s.c. in the hind footpads and in the base of the tail with 25 µg $MBP_{68-86}$, emulsified (1:1 dilution) in 100 µl of CFA containing 2 mg/ml M. tuberculosis (strain H37Ra, BD Diagnostics). Clinical signs were evaluated in a blinded fashion by at least two investigators. Body weight and clinical score were recorded daily (0, healthy; 1, tail paralysis; 2, ataxia and/or paresis of hind limb; 3, paralysis of both of the hind limbs, 4, tetra paralysis; 5, moribund state or death).

RNA purification, cDNA synthesis, reverse transcription PCR, and real-time quantitative PCR analysis. For RNA expression analysis, cells from whole hippocampi were extracted with TRI Reagent (MRC, Cincinnati, Ohio), and total cellular RNA was purified from the lysates using the RNeasy kit (Qiagen, Hilden, Germany). RNA (1 µg) was converted to cDNA using SuperScript II (Promega, Madison, Wis.). The amplification cycle was 95° C. for 5 s, 60° C. for 20 s, and 72° C. for 15 s.

The following primers were used:

```
GAPDH,
                              (SEQ ID NO: 37)
5'-AATGTGTCCGTCGTGGATCTGA-3';
and (SEQ ID NO: 38)
5'-GATGCCTGCTTCACCACCTTCT-3';

KiSS-1,
                              (SEQ ID NO: 39)
5'-AGCTGCTGCTTCTCCTCTGT-3';
and (SEQ ID NO: 40)
5'-GCATACCGCGATTCCTTTT-3'
(Luque et al., 2007);

Total BDNF,
                              (SEQ ID NO: 41)
5'-GCGCCCATGAAAGAAGTAAA-3';
and (SEQ ID NO: 42)
5'-TCGTCAGACCTCTCGAACCT-3';

BDNF 1,
                              (SEQ ID NO: 43)
5'-CCTGCATCTGTTGGGGAGAC-3';
and (SEQ ID NO: 44)
5'-GCCTTGTCCGTGGACGTTTA-3';

BDNF 2,
                              (SEQ ID NO: 45)
5'-CTAGCCACCGGGGTGGTGTAA-3';
and (SEQ ID NO: 46)
5'-AGGATGGTCATCACTCTTCTC-3';

BDNF 3,
                              (SEQ ID NO: 47)
5'-CTTCCTTGAGCCCAGTTCC-3';
and (SEQ ID NO: 48)
5'-CCGTGGACGTTTACTTCTTTC-3';
```

-continued

BDNF 4,
    (SEQ ID NO: 49)
5'-CAGAGCAGCTGCCTTGATGTT-3';
and (SEQ ID NO: 50)
5'-GCCTTGTCCGTGGACGTTTA-3'
(Zajac et al., 2010).

Kisspeptin treatment. Mice were injected i.p with 100 μl of 1/10/100 μM Kp-10 peptide (SEQ ID NO:3) (synthesized at the Weizmann Institute of Science, or Sigma-Aldrich, Israel) dissolved in PBS, 30 minutes before the PPI analysis.

MK-801 treatment. The NMDA receptor antagonist [+]-5-methyl-10,11-dihydro-5H-dibenzo-[a,d]-cyclohepten-5,10-imine hydrogen maleate (MK-801, Sigma) was injected i.p to C57B1/6 mice (0.1 mg/kg) 15 min after injection of Kp-10 and were subject to PPI analysis 15 min later.

Neurotensin receptor antagonist SR142948 (TOCRIS COOKSON LTD) was used at 100 μg/kg 60 min before the PPI analysis.

GnRH receptor antagonist Cetrorelix Acetate (Cetrotide™, Anaspec Inc. Fremont, Calif.). Control mice were administered the same volume of PBS.

Lymphocyte replenishment. Peripheral lymph nodes from adult wild-type or from offspring of poly I:C treated C57B1/6 mice were harvested and mashed. Lymphocytes were resuspended in PBS and injected intravenously to male C57B1/6-SCID mice. Each SCID recipient received cells from one donor mouse. Behavioral assessment was performed 4 weeks after reconstitution, or as indicated in the relevant experiment.

Administration of 5-bromo-2'-deoxyuridine (BrdU) and tissue preparation. Neurogenesis was analyzed as described previously (Ziv et al, 2006). Briefly, mice were injected i.p. with BrdU (Sigma-Aldrich; 50 mg per kg body weight), twice a day for 2 d. They were killed 7 d after the first injection and perfused transcardially. Their brains were removed and postfixed. Free-floating, 30-m-thick coronal hippocampal sections were collected on a freezing microtome (Leica SM2000R) and stored at 4° C. until immunohistochemical analysis.

Antibodies and reagents for immunohistochemistry. To quantify neurogenesis, tissue sections were washed with PBS, incubated in 2N HCl at 37° C. for 30 min, and then blocked for 1 h with blocking solution (PBS containing 20% normal horse serum and 0.5% Triton X-100). The tissue sections were stained overnight with the following primary antibodies: rat anti-BrdU (1:200; Oxford Biotechnology, Kidlington, Oxfordshire, UK) and goat anti-DCX (1:300; Santa Cruz Biotechnology, Santa Cruz, Calif.). Secondary antibodies used were FITC-conjugated donkey anti-goat, and Cy-3-conjugated donkey anti-rat.

Quantification. For microscopic analysis, a Nikon E800 microscope was used. The numbers of labeled cells were counted, by an observer blinded to the identity of the samples, in six coronal sections (370 m apart) per mouse brain. To obtain an estimate of the total number of labeled cells per dentate gyrus, the total number of cells counted in the selected coronal sections from each brain was multiplied by the volume index (the ratio between the volume of the dentate gyrus and the total combined volume of the selected sections).

Statistical analysis. The StatView statistics package was used to perform statistical analysis of all data. PPI experiments were analyzed using two-way analysis of variance (ANOVA) with group treatment and prepulse intensity as the between-subject factors. If no significant interaction was found between the tested groups and the intensities, while significant effects were found with respect to the tested factors themselves, a one-way ANOVA was performed for the single intensities. Only significant main effects were further evaluated using Fisher LSD or two-tailed Student's t-test post hoc analysis. Data from other experiments were analyzed using Student's t-test (for experiments that included two groups) or one-way ANOVA (for experiments that included three groups), with group treatment or immune background as the between subject factor. RAWM measurements were analyzed using two-way analysis of variance (ANOVA) with group treatment as the between-subject factors. Only significant main effects were further evaluated using two-tailed Student's t-test post hoc analysis.

Example 1

Alterations in the Immune Response in a Neurodevelopmental Animal Model for Schizophrenia Sensorimotor gating is an active process that contributes to the ability to segregate a continuous stream of sensory and cognitive information, and to selectively allocate attention to a significant event by silencing the background. The specific features of an individual's gating process are considered to be plastic, and governed by genetic and developmental processes, but also by the environmental milieu, and the neurochemical and hormonal state of the CNS. The sensorimotor gating function may be measured by testing prepulse inhibition (PPI), the phenomenon by which a low-intensity prepulse stimulus attenuates the response to a subsequent startle-eliciting noise (FIG. 1A).

Among the critical environmental factors that have been linked to an increased risk of developing schizophrenia later in life are maternal infections during pregnancy. Since the specificity of the viral infection appears irrelevant to schizophrenia development, poly I:C administration during pregnancy, causing non-specific immune activation, is accepted as a valid animal model for inducing this disease.

Figure 1B:
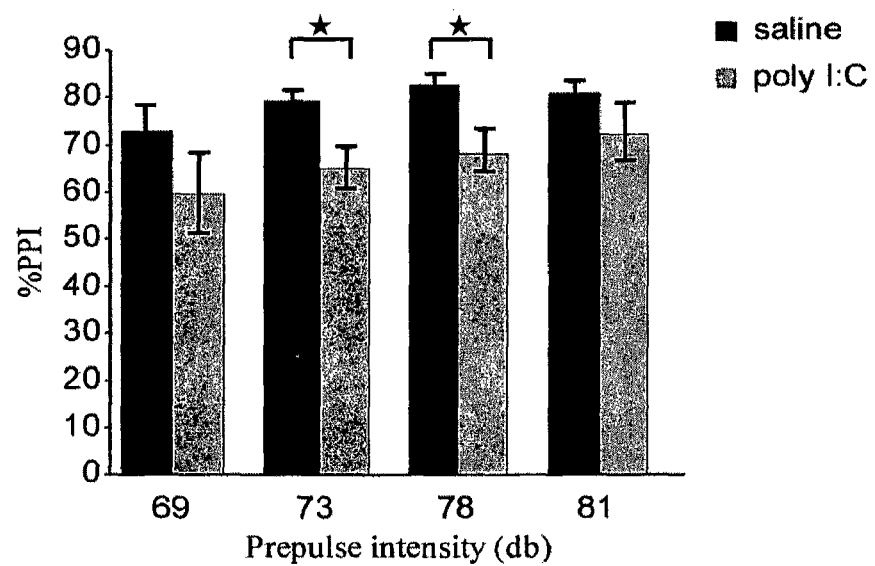

Poly I:C injection into pregnant females is known to cause the emergence of psychopathological behavior in the offspring at early adulthood (Zuckerman et al., 2003). We first utilized this animal model to test whether prenatal infection causes a reduced immune response to self antigens, as previously observed in schizophrenic patients (Kipnis et al., 2006). Pregnant Lewis rats were treated with 4 mg/kg of poly I:C or saline at gestational day 14. Female offspring were tested for PPI at adulthood, to verify the successful induction of schizophrenia-like behavior. As expected, adult offspring of the poly I:C treated rats showed a reduction in PPI compared to the progeny of saline-treated animals (FIG. 1B). To measure alterations in immunity to brain-specific antigens in the poly I:C-affected offspring, we vaccinated female and male offspring at adulthood with the myelin basic protein (MBP)-derived peptide, $MBP_{68-86}$, a CNS-associated self antigen known to be the immune-dominant epitope in this strain (Chou et al., 1979), and examined lymphocyte proliferation in response to the injected antigen, $MBP_{68-86}$, as well as to concanavalin A (Con-A), a lymphocyte mitogen, or to ovalbumin (Ova, an irrelevant antigen). We found, in lymphocytes of the offspring of the poly I:C-treated animals, a significant reduction in the proliferative response to MBP (Table 1). Furthermore, in the poly I:C affected offspring, there was a slightly elevated response to Ova and to Con-A compared to the control, although this difference was not statistically significant (Table 1).

TABLE 1

Lymphocyte proliferation in response to injected antigens

| | prenatal treatment | | |
|---|---|---|---|
| Antigen | saline (PI ± SD) | poly I:C (PI ± SD) | P-value (t-test) |
| MBP$_{68-86}$ | 1.3 ± 0.11 | 1.0 ± 0.11 | 0.01 |
| Ova | 1.0 ± 0.14 | 1.2 ± 0.09 | 0.13 |
| Con-A | 71 ± 49 | 126 ± 67 | 0.15 |

To further examine the CNS-specific immune response in the poly I:C offspring, we tested their susceptibility to experimental autoimmune encephalomyelitis (EAE), the animal model for multiple sclerosis (MS). We expected that if there indeed was a reduction in CNS specific T-cell response in the offspring of poly I:C treated animals, they would be less susceptible to development of EAE upon challenge. In this experiment, we tested only the female offspring, as females are known to be more susceptible to the induction of EAE, and thus any observed effect would be more pronounced. EAE was induced in adult offspring of control or poly I:C-treated rats by immunization with MBP$_{68-86}$ emulsified in CFA, and clinical symptoms of encephalomyelitis were monitored daily. The offspring of poly I:C treated rats showed a delayed onset and a shorter duration of EAE symptoms following MBP$_{68-86}$ vaccination, compared to the controls (Table 2). These results supported our contention that immune activation during pregnancy is associated with reduced immune response to brain antigens in the offspring.

TABLE 2

Onset and duration of EAE in response to MBP injection

| prenatal treatment | saline (day ± SEM) | poly I:C (day ± SEM) | P-value (t-test) |
|---|---|---|---|
| Onset | 10.18 ± 0.2 | 11.17 ± 0.2 | 0.004 |
| Duration | 6.27 ± 0.3 | 5.08 ± 0.3 | 0.005 |

Example 2

Congenital Immune Deficiency Causes Reduced PPI with Onset at Early Adulthood

Figure 2A:
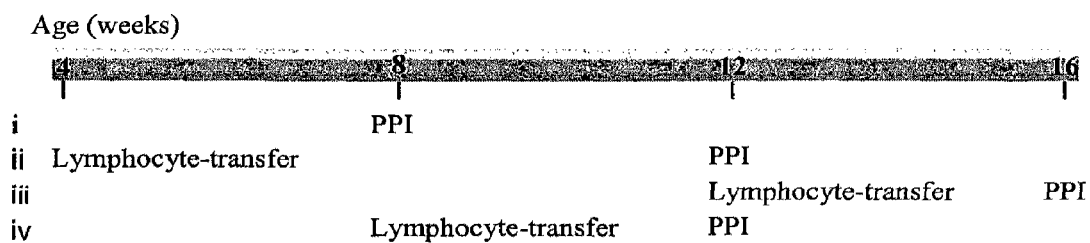
FIGS. 2A-2E show that immune deficiency causes abnormal PPI that is reversible by lymphocyte transfer. (2A) Experimental design showing different ages for lymphocyte transfer and PPI measurements in male C57B1/6 wild-type and severe combined immunodeficiency (SCID) mice. (2B) PPI in adolescent (8 week old) C57BL/6 wild-type (n=18) and SCID (n=16) mice. (Repeated measure ANOVA: groups: $F(1,32)=0.07$, $P=0.79$; prepulse intensities: $F(3,96)=3.49$, $P=0.0186$; groups x prepulse intensities: $F(3,96)=0.04$; $P=0.99$). (2C) PPI in adult (12-week old) C57BL/6 wild-type (n=8), SCID (n=7) and SCID mice that were reconstituted with lymphocytes as juveniles (4 weeks) (n=8) (Repeated measure ANOVA: groups: $F(2,20)=3.59$, $P=0.04$; prepulse intensities: $F(3,60)=1.74$, $P=0.17$; groups x prepulse intensities: $F(6,60)=1.43$; $P=0.22$. One-way ANOVA: 69 dB: $F(2,20)=2.32$, $P=0.12$; 73 dB: $F(2,20)=4.11$, $P=0.03$; 78 dB: $F(2,20)=3.21$, $P=0.06$; 81 dB: $F(2,20)=3.70$, $P=0.04$; *$P<0.05$, Fisher LSD post hoc analysis). (2D) PPI in adult (16 week old) C57B1/6 wild-type (n=8), SCID (n=7) and SCID mice that were reconstituted with lymphocytes as adults (12 weeks) (n=7) (Repeated measure ANOVA: groups: $F(2,19)=3.52$, $P=0.05$; prepulse intensities: $F(3,57)=8.92$, $P=0.0001$; groups x prepulse intensities: $F(6,57)=2.2$; $P=0.06$. One-way ANOVA: 69 dB: $F(2,19)=6.05$, $P=0.01$; 73 dB: $F(2,19)=1.95$, $P=0.17$; 78 dB: $F(2,19)=0.26$, $P=0.77$; 81 dB: $F(2,19)=3.54$, $P=0.04$; *$P<0.05$, Fisher LSD post hoc analysis). (2E) PPI in adult (12 week old) C57B1/6 SCID mice (n=8) compared to SCID mice that were reconstituted with lymphocytes derived from offspring of poly I:C-(n=8) or saline-treated dams (n=8) at the age of 8 weeks (Repeated measure ANOVA: groups: $F(2,21)=3.89$, $P=0.04$; prepulse intensities: $F(3,63)=6.27$, $P=0.001$; groups x prepulse intensities: $F(6,63)=1.82$; $P=0.11$. One-way ANOVA: 69 dB: $F(2,21)=5.56$, $P=0.01$; 73 dB: $F(2,21)=3.46$, $P=0.05$; 78 dB: $F(2,21)=3.52$, $P=0.04$; 81 dB: $F(2,21)-1.11$, $P=0.35$; *$P<0.05$, Fisher LSD post hoc analysis). Values represent means±S.E.M.
Figure 2B:
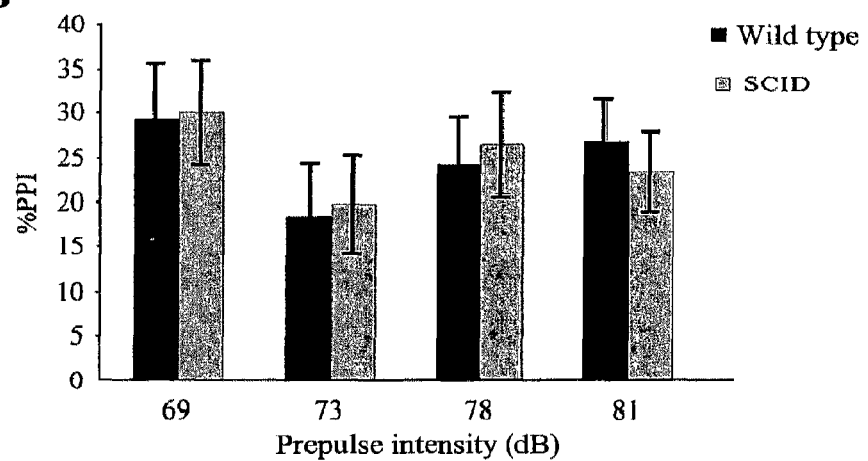

The correlation between the behavioral malfunction and the immune changes induced in the progeny of poly I:C treated animals, prompted us to explore the more general question of whether a congenital immune deficit could cause mental dysfunction that emerges only at adulthood. To this end, we used severe combined immune deficient (SCID) mice, which lack both functional T- and B-lymphocyte populations. SCID mice were previously shown to develop various cognitive abnormalities including impaired hippocampal-dependent spatial memory (Ziv et al., 2006) and increased anxiety levels in response to acute stress. Those abnormal behaviors were attributed to their immune deficiency. Moreover, these mice have reduced hippocampal BDNF levels and reduced neurogenesis. Here, we tested whether PPI in SCID is impaired, and if so, whether its manifestation is age dependent. Adolescent (8 week old) SCID mice showed normal PPI behavior: ANOVA of percent PPI indicated a significant main effect of prepulse intensities, but not of immunological background (FIGS. 2Ai and 2B). However, when the same mice were tested again at early adulthood (12 weeks of age), they showed reduced PPI relative to the age-matched, controls: ANOVA of percent PPI indicated a significant main effect of the immunological background, but not of the prepulse intensities.

Figure 2C:
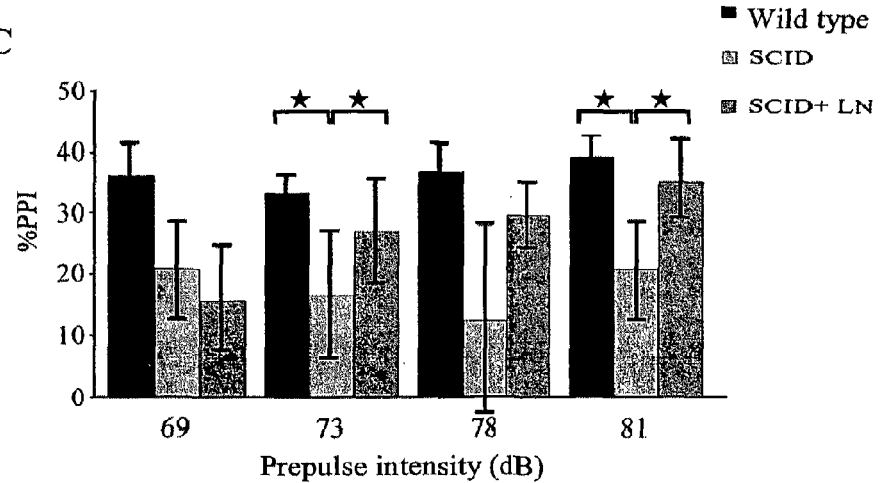
Figure 3A:
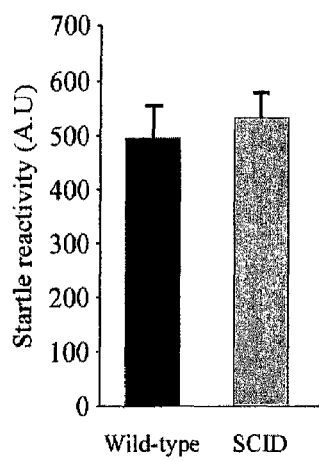
FIGS. 3A-3C show that there are no differences in startle reaction to pulse-alone and prepulse alone trials between SCID and wild-type mice. Startle reaction to pulse alone was tested in wild-type and SCID mice (with and without immune reconstitution), at the age of 8 (3A; $t_{28}=1.69$, $P=0.1$, n=15,16) and 12 weeks (3B; one-way ANOVA: $F(2,21)=0.32$, $P=0.73$, n=7,9,8). (C) Startle reaction to prepulse alone (69 dB) in wild-type and SCID mice ($t_{18}=1.04$, $P=0.31$). Values represent means±S.D.
Figure 3B:
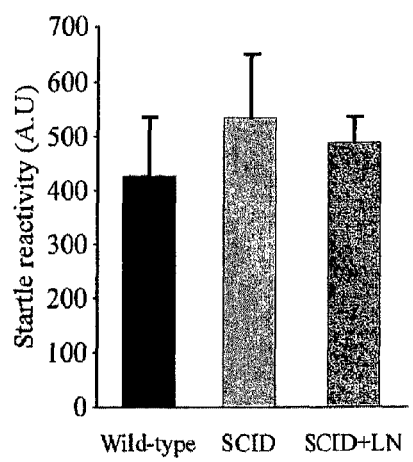
Figure 3C:
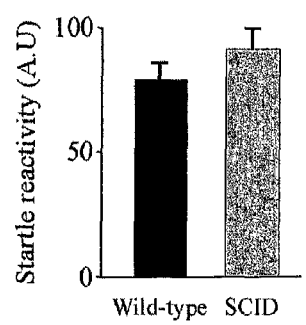

To identify the prepulse intensities at which percent PPI significantly differed between the groups, we examined the performance of the groups at single intensities and found that the differences between SCID and wild-type mice reached statistical significance at prepulse intensities of 73 and 81 dB (FIG. 2C). Importantly, the SCID and wild-type mice did not differ in their startle reactivity to pulse-alone trials nor in their reaction to the prepulse alone trials (FIGS. 3A-3C).

Figure 2D:
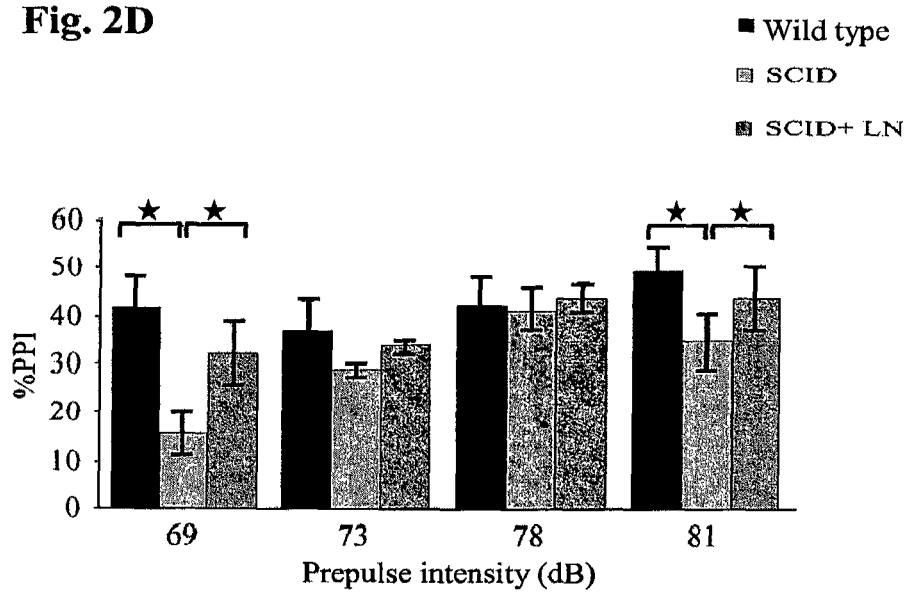

To further demonstrate a causal relationship between the immune deficiency and the observed impairment in the PPI response, we tested whether repopulation with normal lymphocytes could prevent and/or restore the impairment in the PPI. We therefore transferred lymphocytes from wild-type mice to SCID mice either at infancy (4 weeks, FIG. 2Aii) or in adulthood (12 weeks, FIG. 2Aiii). SCID mice that were reconstituted at 4 weeks of age exhibited normal percent PPI levels at both prepulse intensities (73 and 81 dB) in which significant differences were found between SCID and wild-type mice (FIG. 2C). Reconstitution at adulthood (12 weeks) yielded similar results when PPI was examined 4 weeks later: ANOVA of percent PPI indicated a significant main effect of the immunological background, but not of the prepulse intensities (FIG. 2D).

To identify the prepulse intensities at which percent PPI significantly differed between the groups, we examined the performance of the groups at single intensities and found that the differences between SCID and wild-type mice reached statistical significance at prepulse intensities of 69 and 81 dB. Immune reconstitution restored percent PPI to normal at those intensities. These results demonstrate that a congenital immune deficit caused late manifestation of a behavioral abnormality, which could be reversed by immune reconstitution, either at infancy or in adulthood.

Figure 4:
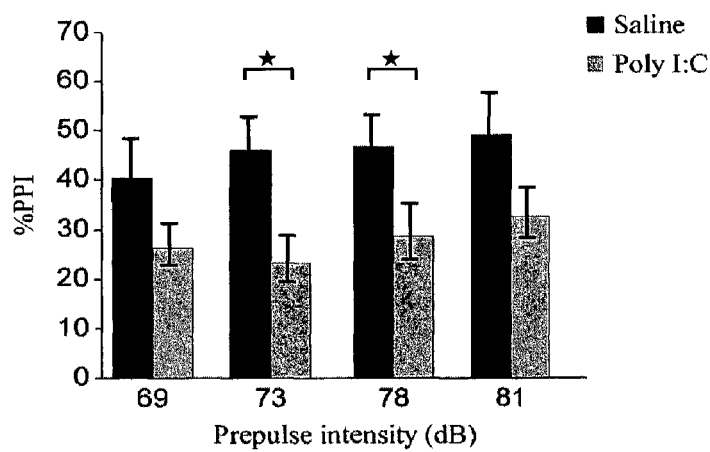
FIG. 4 shows that immune activation with poly I:C during pregnancy caused abnormal PPI in the offspring of C57B1/6 mice. PPI in adult male C57B1/6 offspring of poly I:C-treated dams is reduced compared to PPI in the offspring of saline-treated dams. (n=9) (Repeated measure ANOVA: groups: $F(1,16)=6.33$, $P=0.02$; prepulse intensities: $F(3,48)=2.60$, $P=0.06$; groups x prepulse intensities: $F(3,48)=0.70$; $P=0.56$. One-way ANOVA: 69 dB: $F(1,16)=3.34$, $P=0.09$; 73 dB: $F(1,16)=5.50$, $P=0.03$; 78 dB: $F(1,16)=9.51$, $P=0.01$; 81 dB: $F(1,16)=3.37$, $P=0.08$; *$P<0.05$, Fisher LSD post hoc analysis). Values represent means±S.E.M.

The ability of a normal lymphocyte population to reverse abnormal PPI behavior in immune deficient mice, encouraged us to test whether immune cells derived from the offspring of poly I:C treated dams would reverse the abnormal behavior of SCID mice in the PPI test. We therefore injected 4 mg/kg of poly I:C or saline to pregnant C57B1/6 mice at gestational day 14; after validating that their adult offspring manifested reduced PPI, (FIG. 4), we isolated lymphocytes from these adult offspring and transferred them to adolescent (8 weeks old) naïve SCID mice (FIG. 2A iv). As controls, we transferred lymphocytes from offspring of saline treated dams to another group of SCID mice. At 12-weeks, SCID mice that received lymphocytes from the offspring of poly I:C treated dams showed similar PPI compared to non-reconstituted SCID mice (FIG. 2E); in contrast, the SCID mice that received lymphocytes from offspring of saline treated dams showed improved PPI: ANOVA of percent PPI yielded a significant main effect for the immune background, and the prepulse intensities. However, the interaction between prepulse intensities and immunological background did not reach statistical significance.

Figure 2E:
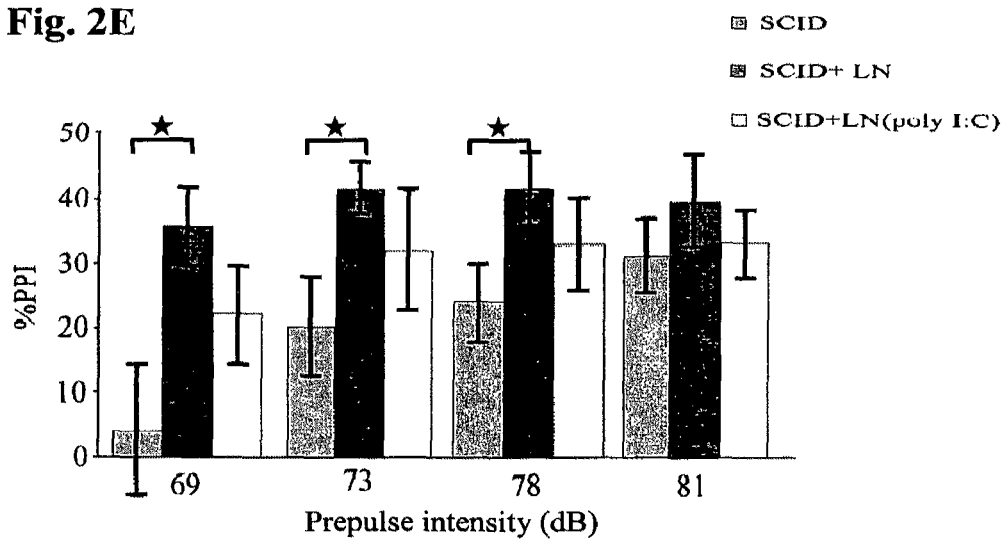

To identify the prepulse intensities at which percent PPI significantly differed between the groups, we examined the performance of the groups at single intensities and found that immune reconstitution with lymphocytes from the offspring of saline treated dams significantly improved percent PPI compared to SCID mice at prepulse intensities of 69, 73 and 78 dB. On the other hand, SCID mice reconstituted with lymphocytes derived from the offspring of poly I:C treated dams did not differ significantly at any of the intensities tested (FIG. 2E). These results further support the observation of abnormal adaptive immunity in the offspring of poly I:C treated dams (Table 1), and strengthen our proposed linkage between this defect and the observed behavioral abnormalities.

Example 3

Figure 5A:
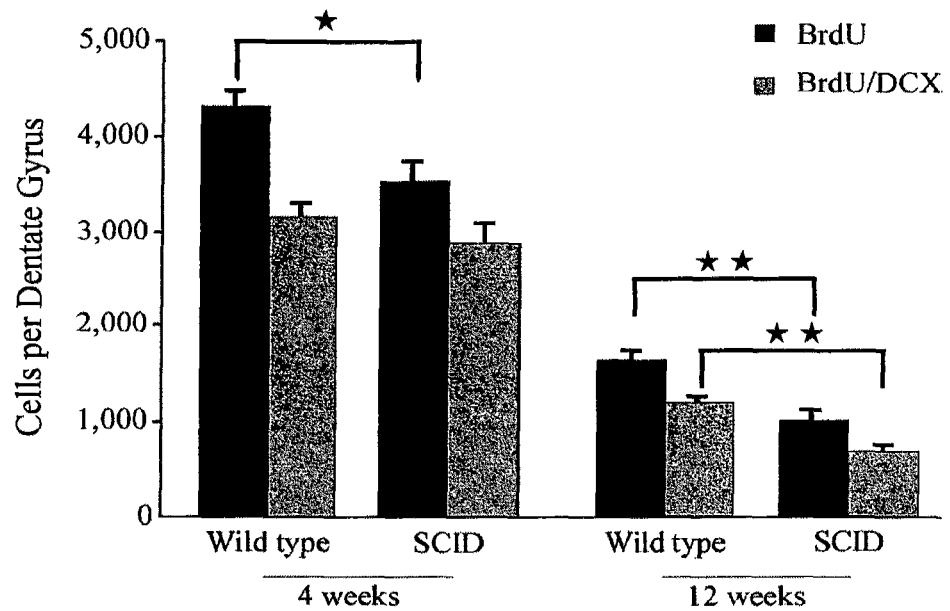
FIGS. 5A-5B show age-dependent differences in neurogenesis between wild-type and immune deficient mice. (5A) Balb/c mice (SCID and wild-type) at 4 weeks and 12 weeks of age were injected with BrdU (see Methods), sacrificed 7 days after the first BrdU injection, and their dentate gyrus was analyzed for BrdU and for BrdU$^+$/DCX$^+$ cells. For 4 week old mice, for BrdU$^+$ cells: $t_8=-3.1$, *$P=0.015$; for BrdU$^+$/DCX$^+$ cells: t8=1.13, $P=0.29$; n=6 and n=4 for wild-type and SCID, respectively; for 12 week old mice, for BrdU cells: $t_6=-5.70$, $P=0.0011$; for BrdU$^+$/DCX$^+$ cells: $t_6=-5.74$ $P=0.0012$; n=4. (5B) Percentage reduction in the number of BrdU$^+$ cells in SCID compared to wild-type mice at 4 and 12 weeks. Calculation: 100%−(percentage of BrdU$^+$ cells in individual SCID from the number of BrdU$^+$ cells in wild-type), ($t_6=3.01$, *$P=0.024$; same groups as in a). Values represent means±S.E.M.
Figure 5B:
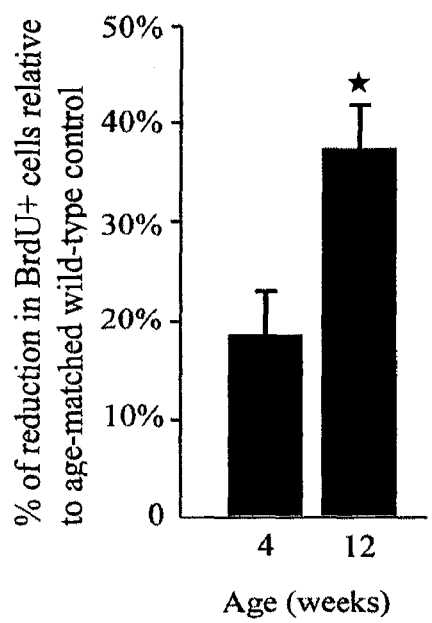

Age-Related Requirements for Immune-Cell Support of Hippocampal Neurogenesis Our previous studies showed that adult SCID mice suffer from impaired neurogenesis (Ziv et al., 2006), another aspect of brain plasticity that is compromised in schizophrenic patients, and in the offspring of poly I:C treated dams. The question that emerged, however, is whether this aspect of brain plasticity in these congenitally immune deficient mice is also mainly manifested at adulthood. Neurogenesis was measured at infancy (4 weeks old) and early adulthood (12 weeks old) in the dentate gyrus of wild-type and SCID mice. All mice received four injections of the cell-proliferation marker, BrdU (every 12 h, i.p.), and labeled cells were analyzed 7 d after the first injection. Their brains were excised and their hippocampi examined immunohistochemically for both BrdU and the early neuronal differentiation marker, doublecortin (DCX). At 4 weeks, a small (18%) reduction in progenitor cell proliferation (BrdU+ cells) was observed in the SCID mice, compared to their wild-type controls (FIG. 5A, left panel). It was noted, however, that SCID mice had a higher neuronal differentiation percentage than wild-type mice (81.3±1.8% and 73.5±1.2%, respectively), and this might account for the apparently similar numbers of newly formed neurons (BrdU+/DCX+ cells) in the two groups. Consistent with previous findings, at 12 weeks, in both mouse groups, there was a reduction in proliferation relative to 4 weeks (FIG. 5A, right panel versus left). Yet, at 12 weeks, cell proliferation diverged between the SCID mice versus their wild-type controls; when cell proliferation was compared at this age, the difference was twice as great as that seen in the infant mice (FIG. 5B). Moreover, at 12 weeks of age, the total number of newly formed neurons (BrdU+/DCX+) was also significantly lower in SCID relative to wild-type mice (FIG. 5A, right panel). These results indicate that impaired neurogenesis in congenitally immune deficient mice is manifested maximally at early adulthood.

Example 4

Kisspeptin Expression Links the Congenital Immune Deficit and Late Onset of Schizophrenic-Like Behavior Changes in sex hormone expression can modulate the brain maturation process during adolescence, and sex hormone expression was found to be abnormal in schizophrenic patients (Gil-Ad et al., 1981). In addition, treatment with sex hormones was proposed as a treatment for schizophrenia (Kulkarni et al., 2001; Elias et al., 2007; Soreni et al., 2004). Based on the known effect of the immune system on sex hormones, we envisioned that the abnormal immunity in schizophrenia might affect brain maturation in part through the impaired regulation of sex hormones. We proposed that kisspeptin, a protein that is considered the gatekeeper for the onset of puberty (de Roux et al., 2003, Seminara et al., 2003) and regulates hippocampal synaptic transmission (Arai 2008; Arai et al., 2005, 2009), might be a potential candidate for the interface between the immune system and brain regulation at this critical period of puberty.

Figure 6A:
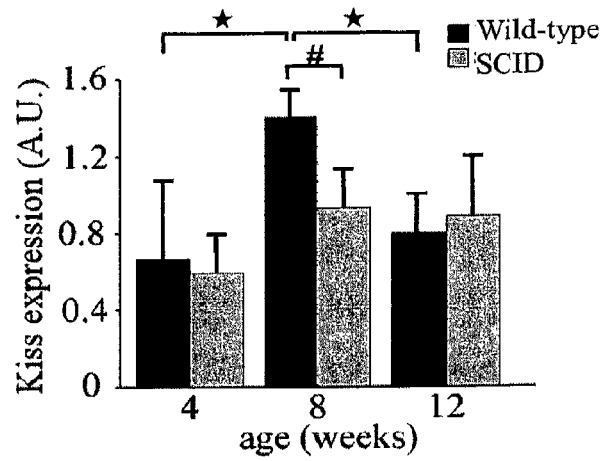
FIGS. 6A-6D show immune regulation of kisspeptin expression in the hippocampus and its relevance to performance in the PPI test. qPCR analysis of KiSS-1 expression in the hippocampus of (6A) wild-type and SCID mice at different ages (one-way ANOVA: wild-type: $F(2,13)=4.11$, $P=0.04$, *$P<0.05$; SCID: $F(2,11)=1.47$, $P=0.27$. Student's t-test: 4 weeks: $t_7=-0.29$, $P=0.78$ (n=5,4); 8 weeks: $t_{6.6}=-2.46$, #$P=0.04$ (n=6,5); 12 weeks: $t_8=0.46$. $P=0.66$ (n=5)), (6B) 8 week old wild-type (n=11), SCID (n=8), and SCID mice that were reconstituted with lymphocytes at 4 weeks of age (n=4) ($F(2,20)=5.25$, $P=0.01$; *$P=0.05$, Fisher LSD post hoc analysis), and (6C) adult male offspring of poly I:C-(n=6) or saline-treated dams (n=6) ($t_{10}=2.24$, *$P=0.04$). Values represent means±SD. (6D) Treatment with Kp-10 (SEQ ID NO: 3) restores the abnormal PPI caused by congenital immune deficiency. PPI in adult male (12 week) C57B1/6J wild-type mice was tested and compared to that of SCID mice injected with PBS and SCID mice that were injected i.p. with Kp-10 (Repeated measure ANOVA: groups: $F(2,35)=4.88$, $P=0.01$; prepulse intensities: $F(6,35)=10.74$, $P=0.0001$; groups x prepulse intensities: $F(6,105)=0.762$, $P=0.6$. One-way ANOVA: 69 dB: $F(2,35)=6.9$, $P=0.003$; 73 dB: $F(2,35)=0.83$, $P=0.44$; 7 dB 8: $F(2,35)=2.01$, $P=0.15$; 8 dB 1: $F(2,35)=2.179$, $P=0.12$; *$P<0.05$, Fisher LSD post hoc analysis). Values represent means±S.E.M.
Figure 6B:
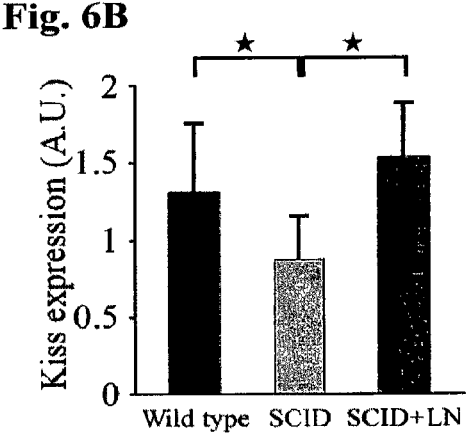
Figure 6C:
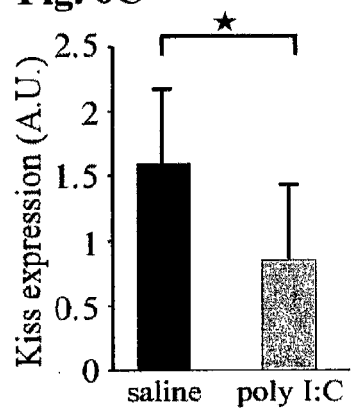

To identify potential immune-dependent regulation of KiSS-1 expression in the hippocampus, we analyzed mRNA levels of KiSS-1 by quantitative real-time PCR (qPCR) in wild-type and SCID mice of different ages. We found that in the hippocampus at 8 weeks of age (puberty), there was a peak in KiSS-1 levels in the wild-type mice, which was absent in the SCID mice (FIG. 6A). Moreover, when SOD mice were replenished with lymphocytes as juveniles (4 weeks of age), their hippocampal KiSS-1 expression level at puberty was restored to normal (FIG. 6B). To further examine whether changes in KiSS-1 may be relevant to schizophrenia, we analyzed KiSS-1 mRNA expression levels in the hippocampus of poly I:C affected offspring, and offspring of control mice. qPCR analysis revealed a reduction in KiSS-1 mRNA levels in adult poly I:C affected mice compared to age-matched controls (FIG. 6C). These results indicated that the immune system regulates KiSS-1 mRNA levels in the hippocampus in adolescence. Moreover, our data indicated that the lack of elevation of KiSS-1 expression in immune-deficient adolescent mice was relevant to the late manifestation of behavioral abnormalities in congenitally immune-compromised mice.

To confirm this possibility we examined whether injection of kisspeptin can restore the abnormal PPI in SCID mice to the normal level in wild-type mice. We analyzed the PPI in adult (12 week old) wild-type mice and, in SCID mice that were injected IP with 100 µl of 100 µM Kp-10 (SEQ ID NO:3), 30 minutes prior to PPI testing. Control SCID mice were treated similarly with PBS. Indeed, we found that SCID mice had reduced PPI relative to the wild-type, however, Kp-10 restored the PPI of SCID mice back to the normal level (FIG. 6D).

Figure 6D:
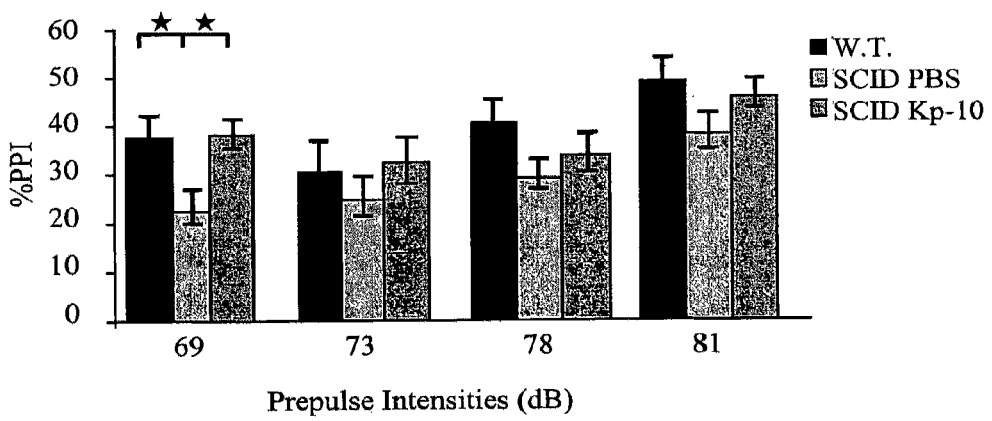

To identify the prepulse intensities in which percent PPI significantly differed between the groups, we examined the performance of the groups at single intensities and found that the differences in percent PPI between SCID mice and SCID mice injected with Kp-10 (SEQ ID NO:3) reached statistical significance at prepulse intensities of 69 and 81 dB (FIG. 6D). These results indicate that Kp-10 is a missing link between immunity and brain plasticity in adolescence with regard to regulation of sensorimotor gating.

Example 5

Administration of Kisspeptin at Adolescence Prevents Psychotic-Like Symptoms at Adulthood in an Animal Model for Schizophrenia The observations in Example 4 above led us to hypothesize that kisspeptin has an endogenous anti-psychotic activity and that administration of the peptide at the critical time of its regulation would prevent development of psychotic symptoms at adulthood. At adolescence (8 weeks), the offspring of poly I:C treated dams received a single i.p injection of Kp-10 (100 µl containing 100 µM of peptide dissolved in PBS). Control mice were injected with PBS. PPI analysis at adulthood (12 weeks) revealed that the Kp-10-treated mice did not exhibit abnormal PPI, compared to the PBS treated mice which showed abnormal PPI. The PPI of the Kp-10 treated mice was similar to the PPI of the normal offspring of saline treated dams (FIG. 7A). As a control we treated naïve animal with single injection of Kp-10 at adolescence, PPI measurement at adulthood revealed no differences between the Kp-10 and the PBS treated mice (FIG. 7B). These results point to a prophylactic effect of Kp-10 on psychotic-like symptoms and further established the link between abnormal KiSS-1 expression and schizophrenia. Similar to our data, it was previously shown that prophylactic treatment with the antipsychotic drug clozapine or Risperidone in peri-adolescence prevented the onset psychotic symptoms and abnormal brain development in poly I:C rat model for schizophrenia (Piontkewitz et al., 2009).

To understand what is the mechanism behind the prophylactic treatment of Kp-10 we examined the expression of total brain-derived neurotrophic factor (BDNF) and its exon transcripts 1-4 according to Zajac et al. (2010). BDNF is a major player in brain development and activity, and was previously shown to be upregulated by Kp-10 in the hippocampus (Arai et al., 2009). Recently, association between a BDNF variant and childhood-onset mood disorder was established (Strauss et al., 2005). Therefore, we studied mRNA expression of a few BDNF transcripts in the hippocampus of offspring of PBS treated dams (n=5) compared to offspring of poly I:C treated dams, which were treated at 8 weeks with either Kp-10 (n=6) or PBS (n=6) (Table 3). The expression level of the whole BDNF did not significantly differ between the groups (Table 3(i)). However, a significant reduction in the expression of BDNF1 transcript was observed in the offspring of poly I:C treated dams. Treatment with Kp-10 at 8 weeks of age induced an increase in the expression of BDNF1 transcript to the normal level (Table 3(ii)). The expression of BDNF2 transcript was elevated in the Kp-10 treated mice compared to the saline treated offspring, but no change was observed in the offspring of poly I:C treated dams compared to the offspring of PBS treated dams (Table 3(iii)). In addition, no significant difference was found between the groups in the expression of BDNF transcripts 3 and 4 (Table 3(iv and v)). These results show that kisspeptin is involved in regulation of hippocampal BDNF levels. The involvement of BDNF in schizophrenia and its effect on PPI levels are still a debate. Our observations of changes in expression of selective forms of BDNF might explain this apparent dichotomy.

TABLE 3

Expression of BDNF transcripts in offspring of saline or poly I:C treated dams, treated with either Kp-10 or PBS

| | | prenatal 8 weeks | | |
|---|---|---|---|---|
| | Transcript | saline PBS | poly I:C PBS | poly I:C Kp-10 | P-value (ANOVA) |
| i | BDNF | 2 ± 0.5 | 1.7 ± 0.6 | 2.4 ± 0.5 | N.S. |
| ii | BDNF1 | *2.3 ± 0.8 | 1.2 ± 0.3 | *2.2 ± 0.5 | 0.01 |
| iii | BDNF2 | 4.6 ± 0.5 | 5.7 ± 0.1 | #6.7 ± 1 | 0.01 |
| iv | BDNF3 | 5.7 ± 1 | 6.2 ± 0.9 | 8 ± 3 | N.S. |
| v | BDNF4 | 7.5 ± 0.9 | 7.4 ± 1 | 9 ± 2 | N.S. |

*$P < 0.05$ student TTST compare to offspring of poly I:C treated dams
$P < 0.05$ student TTST compare to offspring of saline treated dams Example 6

Kisspeptin Restores the Abnormal PPI in Several Animal Models of Schizophrenia

In patients, the diagnosis of schizophrenia usually occurs around early adulthood and therefore it is very unlikely to reach a patient before its formal diagnosis. To determine whether kisspeptin is capable of overcoming the disease symptoms following its onset, we studied the effect of this peptide at adulthood, in several animal models for schizophrenia.

We first examined treatment with Kp-10 (SEQ ID NO:3) in offspring of Poly I:C-treated dams, at adulthood (12 weeks), following the onset of the disease clinical manifestation. Indeed, injection of Kp-10 (SEQ ID NO:3; 100 µl of 100 µM) improved the abnormal PPI in the offsprings of poly I:C treated dams: ANOVA of percent PPI revealed a significant main effect of the treatment, the prepulse intensities and the interaction between the prepulse intensities and the treatment did not reach statistical significance (FIG. 8A).

To further establish the antipsychotic effect of Kp-10, we evaluated its ability to overcome psychotic symptoms induced by the psycho-mimetic agent, MK-801 (N-methyl-D-aspartate (NMDA) antagonist), which induces neurotransmitter imbalance. The acute application of NMDA receptor antagonists, such as MK-801 (non-competitive NMDA antagonist), has been shown to give rise to an acute and short-lasting behavioral state, which mirrors many symptoms of schizophrenia such as, alterations in prepulse inhibition (PPI) and it is considered to be the best pharmacological model of a schizophreniform psychotic episode currently available. C57Bl/6 mice were injected i.p. with Kp-10 (SEQ ID NO:3; 100 µl of 100 µM) or PBS as control 15 min prior to the injection of MK-801 (0.1 mg/kg). 15 min later, mice were subjected to PPI analysis; naive mice were used as a control. Acute administration of MK-801 significantly reduced PPI response while Kp-10 improved the PPI levels in mice which received MK-801 injection (FIG. 8B). ANOVA of percent PPI revealed a significant main effect of the treatment though the prepulse intensities and the interaction between the prepulse intensities and the treatment did not reach statistical significance.

Taken together, these results demonstrate that Kp-10 is able to reverse psychotic-like symptoms in different animal models of schizophrenia, and support the potential use of Kp-10 as an antipsychotic drug.

Example 7

Kisspeptin Improves Behavior Performance in Naïve Mice

Figure 9A:
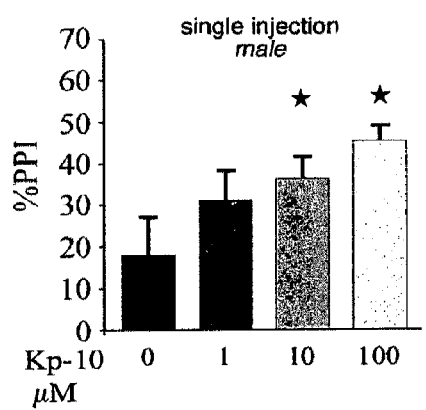
Figure 9B:
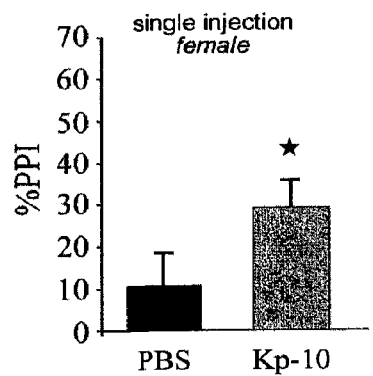

It is commonly accepted that anti-psychotic drugs can elevate PPI in naïve mice, which can be use as a screening test for detecting novel antipsychotic medications. To examine whether Kp-10 can elevate PPI in naïve mice in a dose dependent manner, we analyzed PPI in C57B1/6 mice that were injected i.p with 100 µl of 1/10/100 µM Kp-10 (SEQ ID NO:3). Kp-10 in concentrations of 100 µM and 10 µM significantly increased PPI in naive male mice, as compared to PBS treated mice (FIG. 9A). 1 µM of Kp-10 improved PPI but the improvement was not statistically significant (FIG. 9A). We also examined PPI in a small group of mice that received 100 µl of 1000 µM Kp-10, in this group no improvement was detected as compared to the PBS treated mice (data not shown). Therefore all other experiments in this study were performed with a concentration of 100 µM Kp-10. Since kisspeptin is known to regulate sex hormone secretion, we next examined if Kp-10 can also improve PPI in female mice. Female C57B1/6 mice were treated with a single dose of Kp-10 (SEQ ID NO:3; 100 µl of 100 µM). Indeed, Kp-10 significantly increased the PPI in female mice as well (FIG. 9B).

Figure 9C:
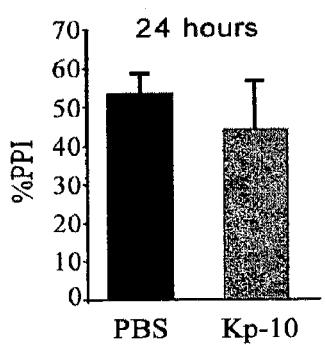
Figure 9D:
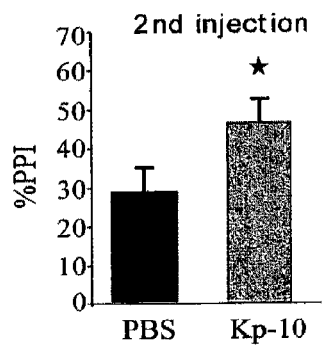
Figure 9E:
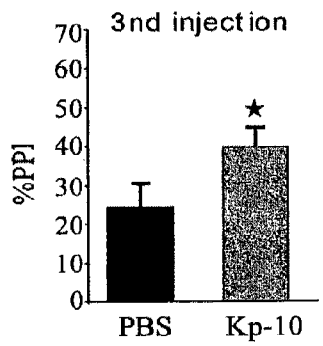

However, the effect of Kp-10 on male mice was transient and lasted for less than 24 hours. When male mice were tested 24 hours after administration of Kp-10, ANOVA of percent PPI revealed no significant main effect of the treatment, the prepulse intensities, and the interaction between the prepulse intensities and the treatment (FIG. 9C). Nevertheless, repeated injections of Kp-10 to male mice 24 hours and 7 days later induced the elevation of the PPI again (FIGS. 9D-9E, respectively). ANOVA of percent PPI revealed a significant main effect of the treatment. The prepulse intensities and the interaction between the prepulse intensities and the treatment did not reach statistical significance. These results further establish the antipsychotic effect of Kp-10.

Example 8

Kisspeptin has an Antidepressive Effect

The results we presented above using the PPI paradigm only relate to the psychotic symptoms of schizophrenia. However, schizophrenia patients suffer from cognitive and negative symptoms as well (i.e depression). Kp-10 was shown to elevate BDNF mRNA levels in hippocampal slices, and thus might affect depression (Arai et al., 2009). To address whether Kp-10 has an antidepressant potency we studied its effect in the tail suspension test, an established method for screening antidepressant-like activity in mice (Steru et al., 1985; Cryan et al., 2005). Naïve mice were treated with Kp-10 (SEQ ID NO:3; 100 µl of 100 µM) or PBS and were subjected to the tail suspension test, in which the mouse is suspended by the tail from a lever, and the movements of the animal are recorded (FIG. 10A). The latency to the first immobility was longer and the duration of the total immobility was shorter in the Kp-10 treated mice compared to PBS treated mice (FIGS. 10B-10C). These results suggest that Kp-10 has potential antidepressant-like activity in mice.

Thus, this study demonstrates that Kp-10 is a novel potential therapeutic agent with antipsychotic and antidepressant properties. The role of kisspeptin in regulation of psychosis may explain the different incidences of schizophrenia in males versus females.

Example 9

Kisspeptin Also Improves Cognitive Functions

One of the cognitive malfunctions in schizophrenia is deficit in spatial learning and memory. To evaluate whether kisspeptine can improve spatial learning and memory, we studied its effect in the radial arm water maze (RAWM), a hippocampal dependent spatial learning and memory assay. In this task, the mouse must find a platform that is located at one of the six maze arms; the time required to reach the platform and the number of errors along the way are recorded (Alamed et al., 2006) (FIG. 11A). Since wild type mice perform well in this test, the ability of Kp-10 to improve their performance is very limited. Therefore we used immune deficient mice (severe combined immunodeficiency; SCID), which have cognitive deficit manifested by poorer performance in the RAWM test. In the beginning of each of the two days experiment the animal received a single Kp-10 (SEQ ID NO:3) injection i.p (100 µl containing 100 µM of peptide dissolved in PBS). Kp-10 (SEQ ID NO:3) administration improved both the latency time to find the platform and reduced the number of errors (FIGS. 11A-11B). These results show that Kp-10 can improve spatial learning and memory indicating its contribution to broad aspects of cognitive functions.

Example 10

Neurotensin and GnRH Antagonist Abolish the Effect of Kp-10 on PPI

To gain some insight into the possible down-stream mechanism of kisspeptin short-term activity on behavior, we studied the effect of a GnRH antagonist on kisspeptin action, since kisspeptin is known as a GnRH activator. We examined the effect of the GnRH receptor antagonist, Cetrorelix Acetate (Cetrotide™), on elevated PPI caused by Kp-10 in naïve animals. Cetrotide™ reversed the effect of Kp-10 on PPI (FIG. 12A). Cetrotide™ alone did not affect PPI (FIG. 12B). This result shows that GnRH is involved in mediating PPI. This result is further supported by previous case report showing that GnRH analog can improve clinical symptoms both positive as well as negative symptoms in schizophrenic patient. Furthermore abnormal sex hormone secretion is known to take place in schizophrenia, and several hormonal-based therapy for schizophrenia, such as estrogen and testosterone, were proposed. Our results further support the potential contribution of sex hormones to the pathophysiology and potential treatments of schizophrenia. In addition, the role of Kisspeptin-GnRH in regulation of psychosis may explain, the different incidences of schizophrenia in males versus females.

Another possible candidate for the down-stream mechanism of kisspeptin is neurotensin, a neuropeptide that is involved in the pathophysiology of schizophrenia and was shown to have antipsychotic actions. Furthermore, neurotensin can be regulated by sex hormone especially estradiol and was suggested to interact with kisspeptin neurons. Therefore, we postulated that the anti-psychotic activity of kisspeptin might be mitigated by neurotensin receptor antagonist. To test this hypothesis we evaluated the effect of neurotensin receptor antagonist (NTA) on the increase in PPI induced by Kp-10 in naïve mice. Although, NTA alone does not affect PPI levels (Binder et al., 2001), in our studies, NTA diminished the effect of Kp-10 on PPI (FIG. 12C). This result suggests that the antipsychotic affect of Kp-10 is mediated in part through regulation of neurotensin.

Beneficial effect of psychiatric drugs such as haloperidol and quetiapine are neurotensin dependent, probably through neurotensin effect on the modulation of dopamine signaling. Dysregulation of the dopaminergic systems is one of the major pathogenesis of schizophrenia. Recently it was suggested that Kisspeptin may have a developmental effect on the dopaminergic system (Vuillermot et al., 2010). Kisspeptin is upstream to neurotensin signaling;therefore our results show that its mechanism of action probably underlies the dopaminergic system.

REFERENCES

Alamed J, Wilcock D M, Diamond D M, Gordon M N, Morgan D. (2006) Two-day radial-arm water maze learning and memory task; robust resolution of amyloid-related memory deficits in transgenic mice. Nat. Protoc. 1(4):1671-9.

Arai A C, Xia Y F, Suzuki E, Kessler M, Civelli O, Nothacker H P. (2005) Cancer metastasis-suppressing peptide metastin upregulates excitatory synaptic transmission in hippocampal dentate granule cells. J Neurophysiol 94(5): 3648-3652.

Arai A C, Orwig N. (2008) Factors that regulate KiSS-1 gene expression in the hippocampus. Brain Res. 1243: 10-18.

Arai A C (2009) The role of kisspeptin and GPR54 in the hippocampus. Peptides 30(1):16-25.

Bilban M, Ghaffari-Tabrizi N, Hintermann E, Bauer S, Molzer S, Zoratti C, Malli R, Sharabi A, Hiden U, Graier W, Knofler M, Andreae F, Wagner O, Quaranta V, Desoye G. (2004) Kisspeptin-10, a KiSS-1/metastin-derived decapeptide, is a physiological invasion inhibitor of primary human trophoblasts. J Cell Sci. 117(Pt 8):1319-28.

Binder E B, Kinkead B, Owens M J, Kilts C D, Nemeroff C B (2001) Enhanced neurotensin neurotransmission is involved in the clinically relevant behavioral effects of antipsychotic drugs: evidence from animal models of sensorimotor gating. J Neurosci 21:601-608.

Castellanos F X, Fine E J, Kaysen D, Marsh W L, Rapoport J L, Hallett M. (1996) Sensorimotor gating in boys with Tourette's syndrome and ADHD: preliminary results. Biol Psychiatry 39(1): 33-41.

Chou C H, Fritz R B, Chou F C, Kibler R F. (1979) The immune response of Lewis rats to peptide 68-88 of guinea pig myelin basic protein. I. T cell determinants. J Immunol 123 (4): 1540-1543.

Cryan J F, Mombereau C, Vassout A (2005) The tail suspension test as a model for assessing antidepressant activity: review of pharmacological and genetic studies in mice. Neurosci Biobehav Rev 29:571-625.

de Roux N, Genin E, Carel J C, Matsuda F, Chaussain J L, Milgrom E. (2003) Hypogonadotropic, hypogonadism due to loss of function of the KiSS-1-derived peptide receptor GPR54. Proc Natl Acad Sci USA 100(19):10972-10976.

Elias A, Kumar A. (2007) Testosterone for schizophrenia. Cochrane Database Syst Rev. (3): CD006197.

Gil-Ad I, Dickerman Z, Weizman R, Weizman A, Tyano S, Laron Z. (1981) Abnormal growth hormone response to LRH and TRH in adolescent schizophrenic boys. Am J Psychiatry 138(3): 357-360.

Gottsch M L, Cunningham M J, Smith J T, Popa S M, Acohido B V, Crowley W F, Seminara S, Clifton D K, Steiner R A. (2004) A role for kisspeptins in the regulation of gonadotropin secretion in the mouse. Endocrinology 145(9): 4073-4077.

Hauben E, Gothilf A, Cohen A, Butovsky O, Nevo U, Smirnov I, Yoles E, Akselrod S, Schwartz M. (2003) Vaccination with dendritic cells pulsed with peptides of myelin basic protein promotes functional recovery from spinal cord injury. J Neurosci 23(25): 8808-8819.

Kipnis J, Cohen H, Cardon M, Ziv Y, Schwartz M. (2004) T cell deficiency leads to cognitive dysfunction: implications for therapeutic vaccination for schizophrenia and other psychiatric conditions. Proc Natl Acad Sci USA 101(21): 8180-8185.

Kipnis J, Cardon M, Strous R D, Schwartz M. (2006). Loss of autoimmune T cells correlates with brain diseases: possible implications for schizophrenia? Trends Mol Med 12(3): 107-112.

Kulkarni J, Riedel A, de Castella A R, Fitzgerald P B, Rolfe T J, Taffe J, Burger H. (2001) Estrogen—a potential treatment for schizophrenia. Schizophr Res. 48(1): 137-144.

Lee J H, Miele M E, Hicks D J, Phillips K K, Trent J M, Weissman B E, Welch D R. (1996) KiSS-1, a Novel Human Malignant Melanoma Metastasis-Suppressor Gene. Journal of the National Cancer Institute 88(23): 1731-1737.

Luque R M, Kineman R D, Tena-Sempere M. (2007) Regulation of hypothalamic expression of KiSS-1 and GPR54 genes by metabolic factors: analyses using mouse models and a cell line. Endocrinology 148(10): 4601-4611.

Niida A, Wang Z, Tomita K, Oishi S, Tamamura H, Otaka A, Navenot J M, Broach J R, Peiper S C, Fujii N. (2006). Design and synthesis of downsized metastin (45-54) analogs with maintenance of high GPR54 agonistic activity. Bioorg Med Chem. Lett. 16(1):134-7.

Ohtaki T, Shintani Y, Honda S, Matsumoto H, Hori A, Kanehashi K, Terao Y, Kumano S, Takatsu Y, Masuda Y, Ishibashi Y, Watanabe T, Asada M, Yamada T, Suenaga M, Kitada C, Usuki S, Kurokawa T, Onda H, Nishimura O, Fujino M. (2001) Metastasis suppressor gene KiSS-1 encodes peptide ligand of a G-protein-coupled receptor. Nature. 411(6837):613-7.

Ornitz E M, Hanna G L, de Traversay J. (1992) Prestimulation-induced startle modulation in attention-deficit hyperactivity disorder and nocturnal enuresis. Psychophysiology 29(4): 437-451.

Piontkewitz Y, Assaf Y, Weiner I (2009) Clozapine administration in adolescence prevents postpubertal emergence of brain structural pathology in an animal model of schizophrenia. Biol Psychiatry 66:1038-1046.

Rothermundt M, Arolt V, Bayer TA. (2001) Review of immunological and immunopathological findings in schizophrenia. Brain Behav Immun 15(4): 319-339.

Seminara S B, Messager S, Chatzidaki E E, Thresher R R, Acierno J S Jr, Shagoury J K, Bo-Abbas Y, Kuohung W, Schwinof K M, Hendrick A G, Zahn D, Dixon J, Kaiser U B, Slaugenhaupt S A, Gusella J F, O'Rahilly S, Carlton M B, Crowley W F Jr, Aparicio S A, Colledge W H. (2003) The GPR54 gene as a regulator of puberty. N Engl J Med 349: 1614-1627.

Soreni N, Weizman A, Weiss M. (2004) Beneficial effects of gonadotropin-releasing hormone analogue treatment on positive and negative symptoms of schizophrenia: a case report. J Clin Psychiatry 65(7): 1020-1021.

Stem L, Chemat R, Thierry B, Simon P (1985) The tail suspension test: a new method for screening antidepressants in mice. Psychopharmacology (Berl) 85:367-370.

Strauss J, Barr C L, George C J, Devlin B, Veto A, Kiss E, Baji I, King N, Shaikh S, Lanktree M, Kovacs M, Kennedy J L. (2005) Brain-derived neurotrophic factor variants are associated with childhood-onset mood disorder: confirmation in a Hungarian sample. Mol. Psychiatry. 10(9):861-7.

Swerdlow N R, Benbow C H, Zisook S, Geyer M A, Braff D L. (1993) A preliminary assessment of sensorimotor gating in patients with obsessive compulsive disorder. Biol Psychiatry 33(4): 298-301.

Swerdlow N R, Paulsen J, Braff D L, Butters N, Geyer M A, Swenson M R. (1995) Impaired prepulse inhibition of acoustic and tactile startle response in patients with Huntington's disease. J Neurol Neurosurg Psychiatry 58(2): 192-200.

Swerdlow N R, Geyer M A. (1998) Using an animal model of deficient sensorimotor gating to study the pathophysiology and new treatments of schizophrenia. Schizophr Bull 24(2): 285-301.

Swerdlow N R, Light G A, Cadenhead K S, Sprock J, Hsieh M H, Braff D L. (2006) Startle gating deficits in a large cohort of patients with schizophrenia: relationship to medications, symptoms, neurocognition, and level of function. Arch Gen Psychiatry 63(12): 1325-1335.

Tomita K, Niida A, Oishi S, Ohno H, Cluzeau J, Navenot J M, Wang Z X, Peiper S C, Fujii N. (2006) Structure-activity relationship study on small peptidic GPR54 agonists. Bioorg Med. Chem. 14(22):7595-603.

Vuillermot S, Weber L, Feldon J, Meyer UA. (2010) longitudinal examination of the neurodevelopmental impact of prenatal immune activation in mice reveals primary defects in dopaminergic development relevant to schizophrenia. J Neurosci 30:1270-1287.

Zajac M S, Pang T Y, Wong N, Weinrich B, Leang L S, Craig J M, Saffery R, Hannan A J. (2010) Wheel running and environmental enrichment differentially modify exon-specific BDNF expression in the hippocampus of wild-type and pre-motor symptomatic male and female Huntington's disease mice. Hippocampus. 20(5):621-36.

Ziv Y, Ron N, Butovsky O, Landa G, Sudai E, Greenberg N, Cohen H, Kipnis J, Schwartz M. (2006) Immune cells contribute to the maintenance of neurogenesis and spatial learning abilities in adulthood. Nat. Neurosci. 9(2): 268-275.

Zuckerman L, Rehavi M, Nachman R, Weiner I. (2003) Immune activation during pregnancy in rats leads to a post-pubertal emergence of disrupted latent inhibition, dopaminergic hyperfunction, and altered limbic morphology in the offspring: a novel neurodevelopmental model of schizophrenia. Neuropsychopharmacology 28(10): 1778-1789.

The invention claimed is:

1. A method for treating schizophrenia or depression or for improvement of cognitive functions, comprising administering to a patient in need thereof an effective amount of the kisspeptin peptide amide of SEQ ID NO: 3.

2. A method for the treatment of a disease or disorder presenting behavioral abnormalities associated with impairment of sensory gating function selected from the group consisting of schizophrenia, Huntington's chorea, obsessive-compulsive disorder (OCD), attention deficit hyperactivity disorder (ADHD), and Tourette's syndrome and/or for treatment of depression, and/or for improving cognitive function, comprising administering to a patient in need thereof an effective amount of a G Protein-coupled Receptor 54 (GPR54) agonist that is the kisspeptin peptide amide of SEQ ID NO: 3 or an analog thereof selected from the group consisting of the peptides of the sequences set forth in SEQ ID NO: 11 to SEQ ID NO: 35, or a salt of said kisspeptin peptide amide of SEQ ID NO: 3 or of said analog thereof.

3. The method according to claim 2, wherein said GPR54 agonist consists of the kisspeptin peptide amide of SEQ ID NO: 3 or a salt thereof.

4. The method according to claim 2 for the treatment of schizophrenia by ameliorating/alleviating the psychotic and/or depression symptoms and the cognitive impairment associated with schizophrenia, which comprises administering to a patient in need thereof an effective amount of the kisspeptin peptide amide of the sequence set forth in SEQ ID NO: 3 or a salt thereof.

5. The method according to claim 4, wherein said treatment comprises administration of the kisspeptin peptide amide of SEQ ID NO:3 or salt thereof in combination with one or more drugs suitable for treatment of schizophrenia selected from the group consisting of clozapine, amisulpride, olanzapine, risperidone, quetiapine, ziprasidone, aripiprazole and paliperidone.

6. The method according to claim 2, for the treatment of a disease or disorder presenting behavioral abnormalities associated with impairment of sensory gating function selected from the group consisting of schizophrenia, Huntington's chorea, obsessive-compulsive disorder (OCD), attention deficit hyperactivity disorder (ADHD), and Tourette's syndrome.

7. The method of claim 6, wherein said disease or disorder presenting behavioral abnormalities associated with impairment of sensory gating function is schizophrenia.

8. The method according to claim 7, wherein said GPR54 agonist is the kisspeptin peptide amide of SEQ ID NO: 3 or a salt thereof.

9. The method of claim 6, wherein said disease or disorder presenting behavioral abnormalities associated with impairment of sensory gating function is selected from the group consisting of Huntington's chorea, obsessive-compulsive disorder (OCD), attention deficit hyperactivity disorder (ADHD), and Tourette's syndrome.

10. The method according to claim 9, wherein said GPR54 agonist is the kisspeptin peptide amide of SEQ ID NO: 3 or a salt thereof.

11. The method according to claim 6, wherein said GPR54 agonist is the kisspeptin peptide amide of SEQ ID NO: 3 or a salt thereof.

12. The method of claim 2, for treatment of depression, and/or for improving cognitive function.

13. The method according to claim 12, wherein said GPR54 agonist is the kisspeptin peptide amide of SEQ ID NO: 3 or a salt thereof.

* * * * *

SEQUENCE LISTING

```
<160> NUMBER OF SEQ ID NOS: 50

<210> SEQ ID NO 1
<211> LENGTH: 145
<212> TYPE: PRT
<213> ORGANISM: Homo sapiens

<400> SEQUENCE: 1

Met Asn Ser Leu Val Ser Trp Gln Leu Leu Phe Leu Cys Ala Thr
1               5                   10                  15

His Phe Gly Glu Pro Leu Glu Lys Val Ala Ser Val Gly Asn Ser Arg
            20                  25                  30

Pro Thr Gly Gln Gln Leu Glu Ser Leu Gly Leu Leu Ala Pro Gly Glu
        35                  40                  45

Gln Ser Leu Pro Cys Thr Glu Arg Lys Pro Ala Ala Thr Ala Arg Leu
    50                  55                  60

Ser Arg Arg Gly Thr Ser Leu Ser Pro Pro Glu Ser Ser Gly Ser
65                  70                  75                  80

Arg Gln Gln Pro Gly Leu Ser Ala Pro His Ser Arg Gln Ile Pro Ala
                85                  90                  95

Pro Gln Gly Ala Val Leu Val Gln Arg Glu Lys Asp Leu Pro Asn Tyr
            100                 105                 110

Asn Trp Asn Ser Phe Gly Leu Arg Phe Gly Lys Arg Glu Ala Ala Pro
        115                 120                 125

Gly Asn His Gly Arg Ser Ala Gly Arg Gly Trp Gly Ala Gly Ala Gly
    130                 135                 140

Gln
145

<210> SEQ ID NO 2
<211> LENGTH: 54
<212> TYPE: PRT
<213> ORGANISM: Artificial Sequence
<220> FEATURE:
<223> OTHER INFORMATION: Synthetic

<400> SEQUENCE: 2

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 3
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION
```

<400> SEQUENCE: 3

Tyr Asn Trp Asn Ser Phe Gly Leu Arg Phe
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (13)..(13)
<223> OTHER INFORMATION: AMIDATION

<400> SEQUENCE: 4

Leu Pro Asn Tyr Asn Trp Asn Ser Phe Gly Leu Arg Phe
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (14)..(14)
<223> OTHER INFORMATION: AMIDATION

<400> SEQUENCE: 5

Asp Leu Pro Asn Tyr Asn Trp Asn Ser Phe Gly Leu Arg Phe
1               5                   10

<210> SEQ ID NO 6
<211> LENGTH: 30
<212> TYPE: PRT
<213> ORGANISM: Artificial Sequence
<220> FEATURE:
<223> OTHER INFORMATION: Synthetic

<400> SEQUENCE: 6

Gln Ile Pro Ala Pro Gln Gly Ala Val Leu Val Gln Arg Glu Lys Asp
1               5                   10                  15

Leu Pro Asn Tyr Asn Trp Asn Ser Phe Gly Leu Arg Phe Gly
            20                  25                  30

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Glu Lys Asp Leu Pro Asn Tyr Asn Trp Asn Ser Phe Gly Leu Arg Phe
1               5                   10                  15

Gly

<210> SEQ ID NO 8
<211> LENGTH: 29
<212> TYPE: PRT
<213> ORGANISM: Artificial Sequence
<220> FEATURE:
<223> OTHER INFORMATION: Synthetic

<400> SEQUENCE: 8

```
Ile Pro Ala Pro Gln Gly Ala Val Leu Val Gln Arg Glu Lys Asp Leu
1               5                   10                  15

Pro Asn Tyr Asn Trp Asn Ser Phe Gly Leu Arg Phe Gly
            20                  25
```

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

```
Lys Asp Leu Pro Asn Tyr Asn Trp Asn Ser Phe Gly Leu Arg Phe Gly
1               5                   10                  15
```

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

```
Trp Asn Ser Phe Gly Leu Arg Phe Gly
1               5
```

<210> SEQ ID NO 11
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 11

```
Ala Asn Trp Asn Ser Phe Gly Leu Arg Phe
1               5                   10
```

<210> SEQ ID NO 12
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 12

```
Tyr Ala Trp Asn Ser Phe Gly Leu Arg Phe
1               5                   10
```

<210> SEQ ID NO 13
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 13

```
Tyr Asn Ala Asn Ser Phe Gly Leu Arg Phe
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 14

Tyr Asn Trp Ala Ser Phe Gly Leu Arg Phe
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 15

Tyr Asn Trp Asn Ala Phe Gly Leu Arg Phe
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 16

Tyr Asn Trp Asn Ser Ala Gly Leu Arg Phe
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 17

Tyr Asn Trp Asn Ser Phe Ala Leu Arg Phe
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: (10)..(10)
<223> OTHER INFORMATION: AMIDATION

<400> SEQUENCE: 18

Tyr Asn Trp Asn Ser Phe Gly Ala Arg Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 19

Tyr Asn Trp Asn Ser Phe Gly Leu Ala Phe
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 20

Tyr Asn Trp Asn Ser Phe Gly Leu Arg Ala
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 21

Phe Asn Trp Asn Ser Phe Gly Leu Arg Phe
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 22

Tyr Asp Trp Asn Ser Phe Gly Leu Arg Phe
1               5                   10

<210> SEQ ID NO 23
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 23

Tyr Asn Trp Asp Ser Phe Gly Leu Arg Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 24

Tyr Asn Trp Asn Thr Phe Gly Leu Arg Phe
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 25

Tyr Asn Trp Asn Ser Tyr Gly Leu Arg Phe
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 26

Tyr Asn Trp Asn Ser Phe Gly Ile Arg Phe
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 27

Tyr Asn Trp Asn Ser Phe Gly Leu Lys Phe
```

```
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (10)..(10)
<223> OTHER INFORMATION: AMIDATION

<400> SEQUENCE: 28

```
Tyr Asn Trp Asn Ser Phe Gly Leu Arg His
1               5                   10
```

<210> SEQ ID NO 29
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MOD_RES
<222> LOCATION: (10)..(10)
<223> OTHER INFORMATION: AMIDATION

<400> SEQUENCE: 29

```
Tyr Asn Trp Asn Ser Phe Gly Leu Arg Phe
1               5                   10
```

<210> SEQ ID NO 30
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: D-Phe
<220> FEATURE:
<221> NAME/KEY: MOD_RES
<222> LOCATION: (10)..(10)
<223> OTHER INFORMATION: AMIDATION

<400> SEQUENCE: 30

```
Tyr Asn Trp Asn Ser Phe Gly Leu Arg Phe
1               5                   10
```

<210> SEQ ID NO 31
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: D-Phe
<220> FEATURE:
<221> NAME/KEY: MOD_RES
<222> LOCATION: (10)..(10)
<223> OTHER INFORMATION: AMIDATION

<400> SEQUENCE: 31

```
Tyr Asn Trp Asn Ser Phe Gly Leu Arg Phe
```

```
<210> SEQ ID NO 32
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is artificial amino acid, Bis(Py)-Amb,
      wherein Amb is 4-(aminomethyl) benzoic acid
<220> FEATURE:
<221> NAME/KEY: MOD_RES
<222> LOCATION: (6)..(6)
<223> OTHER INFORMATION: AMIDATION

<400> SEQUENCE: 32

Xaa Phe Gly Leu Arg Trp
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is artificial amino acid, Gu-Amb, wherein Amb
      is 4-(aminomethyl) benzoic acid and Gu is 1-methyl-guanidine
<220> FEATURE:
<221> NAME/KEY: MOD_RES
<222> LOCATION: (6)..(6)
<223> OTHER INFORMATION: AMIDATION

<400> SEQUENCE: 33

Xaa Phe Gly Leu Arg Trp
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACYLATION
<220> FEATURE:
<221> NAME/KEY: MOD_RES
<222> LOCATION: (8)..(8)
<223> OTHER INFORMATION: AMIDATION

<400> SEQUENCE: 34

Trp Asn Arg Phe Gly Leu Arg Trp
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is artificial amino acid, H-Amb-Nal(2),
      wherein Amb is 4-(aminomethyl) benzoic acid and Nal is 2-amino-
      3-(napht-2-yl) propanoic acid.
```

```
<220> FEATURE:
<221> NAME/KEY: MOD_RES
<222> LOCATION: (5)..(5)
<223> OTHER INFORMATION: AMIDATION

<400> SEQUENCE: 35

Xaa Gly Leu Arg Trp
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic

<400> SEQUENCE: 36

Tyr Gly Ser Leu Pro Gln Lys Ser Gln Arg Ser Gln Asp Glu Asn Pro
1               5                   10                  15

Val

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
aatgtgtccg tcgtggatct ga                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gatgcctgct tcaccacctt ct                                              22

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
agctgctgct tctcctctgt                                                 20

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
gcataccgcg attcctttt                                                  19

<210> SEQ ID NO 41
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 41
gcgcccatga aagaagtaaa                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
tcgtcagacc tctcgaacct                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
cctgcatctg ttggggagac                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
gccttgtccg tggacgttta                                              20

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
ctagccaccg gggtggtgta a                                            21

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
aggatggtca tcactcttct c                                            21

<210> SEQ ID NO 47
<211> LENGTH: 19
<212> TYPE: DNA
<213> ORGANISM: Artificial Sequence
<220> FEATURE:
<223> OTHER INFORMATION: Synthetic

<400> SEQUENCE: 47
cttccttgag cccagttcc                                               19

<210> SEQ ID NO 48
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 48
ccgtggacgt ttacttcttt c                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
cagagcagct gccttgatgt t                                              21

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
gccttgtccg tggacgttta                                                20
```